United States Patent
Nichols et al.

(10) Patent No.: US 11,312,684 B1
(45) Date of Patent: Apr. 26, 2022

(54) PHARMACEUTICALLY ACCEPTABLE SALTS OF PSILOCIN AND USES THEREOF

(71) Applicant: Eleusis Therapeutics US, Inc., New York, NY (US)

(72) Inventors: David E. Nichols, Chapel Hill, NC (US); Graham Johnson, Sanbornton, NH (US); Hooshang S. Zavareh, Cambridge (GB); Claire Wombwell, Cambridge (GB); Daniel Rixson, Cambridge (GB); Peter Haddow, Cambridge (GB); Carrie Sheard, Cambridge (GB); Alexander Schwarz, Baltimore, MD (US)

(73) Assignee: Eleusis Therapeutics US, Inc., New York, NY (US)

( * ) Notice: Subject to any disclaimer, the term of this patent is extended or adjusted under 35 U.S.C. 154(b) by 0 days.

(21) Appl. No.: 17/520,275

(22) Filed: Nov. 5, 2021

Related U.S. Application Data

(60) Provisional application No. 63/148,052, filed on Feb. 10, 2021.

(51) Int. Cl.
*C07D 209/16* (2006.01)
*A61K 31/4045* (2006.01)
*C07C 63/08* (2006.01)

(52) U.S. Cl.
CPC ........ *C07D 209/16* (2013.01); *A61K 31/4045* (2013.01); *C07C 63/08* (2013.01)

(58) Field of Classification Search
CPC .................................................. C07D 209/16
See application file for complete search history.

(56) References Cited

U.S. PATENT DOCUMENTS

| | | | |
|---|---|---|---|
| 7,790,762 B2 | 9/2010 | Day et al. |
| 10,183,001 B1 | 1/2019 | King et al. |
| 10,478,429 B2 | 11/2019 | Hughey et al. |
| 10,485,967 B2 | 11/2019 | Sameti et al. |
| 10,626,105 B2 | 4/2020 | Zhang |
| 10,881,606 B2 | 1/2021 | Schmitz et al. |
| 10,881,607 B2 | 1/2021 | Schmitz et al. |
| 2004/0110828 A1 | 6/2004 | Chowdhury et al. |
| 2006/0135585 A1 | 6/2006 | Day et al. |
| 2011/0060037 A1 | 3/2011 | Woldbye et al. |
| 2011/0104305 A1 | 5/2011 | Day et al. |
| 2011/0111029 A1 | 5/2011 | Schmitz et al. |
| 2012/0028960 A1 | 2/2012 | King et al. |
| 2016/0303361 A1 | 10/2016 | Sameti et al. |
| 2018/0021326 A1 | 1/2018 | Stamets |
| 2018/0079742 A1 | 3/2018 | Zhang |
| 2019/0105313 A1 | 4/2019 | Stamets |
| 2019/0192498 A1 | 6/2019 | Stamets |
| 2019/0225612 A1 | 7/2019 | Semple et al. |
| 2019/0350949 A1 | 11/2019 | Kucuksen et al. |
| 2020/0046963 A1 | 2/2020 | Sameti et al. |
| 2020/0060997 A1 | 2/2020 | Goren et al. |
| 2020/0113819 A1 | 4/2020 | Schmitz et al. |
| 2020/0290992 A1 | 9/2020 | Zhang |
| 2020/0330405 A1 | 10/2020 | Foster et al. |
| 2020/0370073 A1 | 11/2020 | Leo |
| 2020/0375967 A1 | 12/2020 | Stamets |
| 2020/0397752 A1 | 12/2020 | Perez Castillo et al. |

FOREIGN PATENT DOCUMENTS

| | | |
|---|---|---|
| WO | WO-2009/112033 A1 | 9/2009 |
| WO | WO-2009/153019 A1 | 12/2009 |
| WO | WO-2015/090583 A1 | 6/2015 |
| WO | WO-2015/127556 A1 | 9/2015 |
| WO | WO-2015/127558 A1 | 9/2015 |
| WO | WO-2016/161138 A1 | 10/2016 |
| WO | WO-2018/057576 A1 | 3/2018 |
| WO | WO-2018/204354 A1 | 11/2018 |
| WO | WO-2019/073379 A1 | 4/2019 |
| WO | WO-2019/081942 A1 | 5/2019 |
| WO | WO-2019/246532 A1 | 12/2019 |
| WO | WO-2020/023084 A1 | 1/2020 |
| WO | WO-2020/157569 A1 | 8/2020 |
| WO | WO-2020/212952 A1 | 10/2020 |
| WO | PCT/US2021/041321 | 7/2021 |

OTHER PUBLICATIONS

FDA mulls drug to slow late-stage Alzheimer's [online] retrieved from the internet,Sep. 24, 2003, URLhttp://www.cnn.com/2003/HEALTH/conditions/09/24/alzheimers.drug.ap/index.html.*
Cecil Textbook of Medicine, 20th edition (1996), vol. 2, pp. 2050-2057.*
Cecil Textbook of Medicine, 20thedition (1996), vol. 2, pp. 1992-1996.*
International Search Report and Written Opinion for International Application No. PCT/US2021/041321, dated Oct. 26, 2021 (11 pages).

* cited by examiner

*Primary Examiner* — Shawquia Jackson
(74) *Attorney, Agent, or Firm* — Clark & Elbing LLP

(57) ABSTRACT

The present invention composition features pharmaceutically acceptable salts of psilocin and compositions thereof. The pharmaceutically acceptable salts of psilocin may be used to treat a disease or condition, such as a neurological injury, an inflammatory condition, chronic pain, or a psychological condition, in a subject in need thereof.

17 Claims, 15 Drawing Sheets

PHARMACEUTICALLY ACCEPTABLE SALTS OF PSILOCIN AND USES THEREOF

BACKGROUND

Significant interest in the therapeutic application of psilocin has developed, based upon evidence of possible therapeutic effects in a wide array of clinical applications, including psychiatric conditions, pain disorders, and neurological conditions. However, due to the physical properties of psilocin in the solid state, e.g., poor crystallinity with limited enhancement of bulk purity upon crystallization, susceptibility to auto catalyzed oxidation upon handling and prolonged storage, and low water solubility, there exists a need for psilocin salts and formulations with improved stability, physical properties, and handling characteristics.

SUMMARY OF THE INVENTION

The invention features a pharmaceutically acceptable salt of psilocin, wherein the pharmaceutically acceptable salt is a 1:1 benzoate salt.

In another aspect, the invention features a pharmaceutically acceptable salt of psilocin, wherein the pharmaceutically acceptable salt is a 1:1 tartrate salt.

In a further aspect, the invention features a pharmaceutically acceptable salt of psilocin, wherein the pharmaceutically acceptable salt is a 2:1 succinate salt.

In another aspect, the invention features a pharmaceutically acceptable salt of psilocin, wherein the pharmaceutically acceptable salt is a 2:1 salt of 1,5-naphthalenedisulfonic acid, a 1:1 salt of 1,5-naphthalenedisulfonic acid, or a mixture thereof.

In a related aspect, the invention features a pharmaceutical composition including a psilocin salt of the invention and a pharmaceutically acceptable excipient. The pharmaceutically acceptable excipient can be any pharmaceutically acceptable excipient described herein.

In another aspect, the invention features a pharmaceutical composition including (i) an aqueous solution having a pH of between about 3 and about 9 (e.g., 3±1, 4±1, 5±1, 6±1, 7±1, 8±1, and 9±1) and (ii) between about 0.1 mg/mL and about 50 mg/mL (e.g., 0.1±0.1 mg/mL, 0.2±0.1 mg/mL, 0.3±0.1 mg/mL, 0.4±0.1 mg/mL, 0.5±0.5 mg/mL, 1±0.5 mg/mL, 2±1 mg/mL, 3±1 mg/mL, 4±1 mg/mL, 5±1 mg/mL, 6±1 mg/mL, 7±1 mg/mL, 8±1 mg/mL, 9±1 mg/mL, 10±1 mg/mL, 11±1 mg/mL, 12±1 mg/mL, 13±1 mg/mL, 14±1 mg/mL, 15±1 mg/mL, 16±1 mg/mL, 17±1 mg/mL, 18±1 mg/mL, 19±1 mg/mL, 25±5 mg/mL, 30±5 mg/mL, 35±5 mg/mL, 40±5 mg/mL, 45±5 mg/mL, and 50±5 mg/mL) of any one of pharmaceutically acceptable salts of psilocin described herein. The aqueous pharmaceutical composition can be suitable for infusion into a subject for treating a disease or condition described herein.

In some embodiments, the aqueous solution has between about 1 mg/mL and about 15 mg/mL (e.g., 2±1 mg/mL, 3±1 mg/mL, 4±1 mg/mL, 5±1 mg/mL, 6±1 mg/mL, 7±1 mg/mL, 8±1 mg/mL, 9±1 mg/mL, 10±1 mg/mL, 11±1 mg/mL, 12±1 mg/mL, 13±1 mg/mL, 14±1 mg/mL, and 15±1 mg/mL) of any one of pharmaceutically acceptable salts of psilocin described herein.

In another aspect, the invention features a crystal form of a 2:1 succinate salt of psilocin having at least four, five, six, or seven peaks at diffraction angle 2θ(°) as provided in FIG. 4 (SUC Pattern 4) as measured by X-ray powder diffractometry.

In a related aspect, the invention features a crystal form of a 1,5-naphthalenedisulfonic acid salt of psilocin having at least four, five, six, or seven peaks at diffraction angle 2θ(°) as provided in FIG. 7 or FIG. 14 (NAP Pattern 1) as measured by X-ray powder diffractometry.

In a further aspect, the invention features a crystal form of a 1:1 tartrate salt of psilocin having at least four, five, six, or seven peaks at diffraction angle 2θ(°) as provided in FIG. 9 or FIG. 12 (TAR Pattern 3) as measured by X-ray powder diffractometry.

In another aspect, the invention features a crystal form of a 1:1 tartrate salt of psilocin having at least four, five, six, or seven peaks at diffraction angle 2θ(°) as provided in FIG. 10 (TAR Pattern 4) as measured by X-ray powder diffractometry.

In a related aspect, the invention features a crystal form of a 1:1 tartrate salt of psilocin having at least four, five, six, or seven peaks at diffraction angle 2θ(°) selected from 6.7±0.5, 12.6±0.5, 13.4±0.5, 14.7±0.5, 15.8±0.5, 16.2±0.5, 17.2±0.5, 18.8±0.5, 19.9±0.5, 20.8±0.5, 21.8±0.5, 22.5±0.5, 23.4±0.5, 23.7±0.5, 24.7±0.5, 25.5±0.5, 26.5±0.5, 27.0±0.5, 28.5±0.5, and 29.4±0.5 (TAR Pattern 1) as measured by X-ray powder diffractometry.

In a further aspect, the invention features a crystal form of a 2:1 succinate salt of psilocin having at least four, five, six, or seven peaks at diffraction angle 2θ(°) selected from 9.7±0.5, 11.2±0.5, 12.3±0.5, 13.8±0.5, 15.9±0.5, 16.4±0.5, 19.4±0.5, 20.0±0.5, 21.3±0.5, 22.6±0.5, 23.3±0.5, 23.5±0.5, 23.8±0.5, 24.5±0.5, 24.7±0.5, 25.0±0.5, 28.0±0.5, 28.3±0.5, 29.0±0.5, and 29.4±0.5 (SUC Pattern 3) as measured by X-ray powder diffractometry.

In a related aspect, the invention features a crystal form of a 1:1 benzoate salt of psilocin having at least four, five, six, or seven peaks at diffraction angle 2θ(°) 9.4±0.5, 10.9±0.5, 12.3±0.5, 13.3±0.5, 14.5±0.5, 15.3±0.5, 16.3±0.5, 16.4±0.5, 18.2±0.5, 18.9±0.5, 19.3±0.5, 19.7±0.5, 20.0±0.5, 20.8±0.5, 21.3±0.5, 21.9±0.5, 22.6±0.5, 22.9±0.5, 23.8±0.5, 24.1±0.5, 24.9±0.5, 25.6±0.5, 26.0±0.5, 26.3±0.5, 26.5±0.5, 26.9±0.5, 27.5±0.5, and 28.5±0.5 (BEN Pattern 1) as measured by X-ray powder diffractometry.

In a related aspect, the invention features a pharmaceutical composition including a crystal form of the invention and a pharmaceutically acceptable excipient. The pharmaceutically acceptable excipient can be any pharmaceutically acceptable excipient described herein. In some embodiments, any one of the pharmaceutical compositions described herein is stored in a container that shields the pharmaceutical composition from exposure to light, such as an amber glass bottle, or an ambient light impermeable container.

In a related aspect, the invention features a method of treating a disease or condition in a subject in need thereof, the method including administering to the subject a psilocin salt of the invention in an amount sufficient to treat the disease or condition. The disease or condition can be a neurological injury, neurodegenerative disease, an inflammatory condition, chronic pain, or a psychological condition. In certain embodiments, the disease or condition is an inflammatory condition (e.g., lung inflammation, neuroinflammation, rheumatoid arthritis, atherosclerosis, psoriasis, type II diabetes, inflammatory bowel disease, Crohn's disease, multiple sclerosis, and/or septicemia). In particular embodiments, the inflammatory condition is chronic obstructive pulmonary disease (COPD), or Alzheimer's disease. In certain embodiments, the disease or condition is a neurological injury (e.g., a stroke, a traumatic brain injury, or a spinal cord injury). In some embodiments, the disease or condition is chronic pain (e.g., pain resulting from postoperative pain, tension headaches, chronic lower back pain, fibromyalgia, nephropathy, multiple sclerosis, shingles, complex regional pain syndrome, cephalic pain, or sciatica). In particular embodiments, the chronic pain condition results from trigeminal autonomic cephalalgia (e.g., episodic and chronic cluster headache (CH), episodic and chronic paroxysmal hemicrania (PH), and short-lasting unilateral neuralgiform headache attacks with conjunctival injection and tearing (SUNCT)). In some embodiments, the trigeminal autonomic cephalalgia is episodic or chronic CH. In certain embodiments, the condition is a psychological condition (e.g., depression, anxiety, addiction, post-traumatic stress disorder, an eating disorder, or compulsive behavior). In particular embodiments, the psychological condition is depression or anxiety.

Definitions

To facilitate the understanding of this invention, a number of terms are defined below and throughout the disclosure. Unless otherwise defined, all technical and scientific terms used herein have the same meaning as commonly understood by one of ordinary skill in the art to which this invention belongs. The terminology herein is used to describe specific embodiments of the invention, but their usage does not limit the invention, except as outlined in the claims.

Terms such as "a", "an," and "the" are not intended to refer to only a singular entity but include the general class of which a specific example may be used for illustration.

As used herein, the term "about" refers to a value that is within 10% above or below the value being described.

The term "administration" or "administering" refers to a method of giving a dosage of a compound or pharmaceutical composition to a subject.

As used herein, the terms "pharmacologically effective amount," "therapeutically effective amount," and the like, when used in reference to a therapeutic composition, refer to a quantity sufficient to, when administered to the subject, including a mammal, for example a human, effect beneficial or desired results, such as clinical results. For example, in the context of treating depression, described herein, these terms refer to an amount of the composition sufficient to achieve a treatment response as compared to the response obtained without administration of the composition. The quantity of a given composition described herein that will correspond to such an amount may vary depending upon various factors, such as the given agent, the pharmaceutical formulation, the route of administration, the type of disease or disorder, the identity of the subject (e.g., age, sex, weight) or host being treated, and the like. An "effective amount," "pharmacologically effective amount," or the like, of a composition of the present disclosure, also include an amount that results in a beneficial or desired result in a subject as compared to a control.

As used herein, the terms "treat," "treating," or "treatment" refer to administration of a compound or pharmaceutical composition for a therapeutic purpose. To "treat a disorder" or use for "therapeutic treatment" refers to administering treatment to a patient already suffering from a disease to ameliorate the disease or one or more symptoms thereof to improve the patient's condition (e.g., by reducing one or more symptoms of inflammation). The term "therapeutic" includes the effect of mitigating deleterious clinical effects of certain inflammatory processes (i.e., consequences of the inflammation, rather than the symptoms of inflammation). The methods of the invention can be used as a primary prevention measure, i.e., to prevent a condition or to reduce the risk of developing a condition. Prevention refers to prophylactic treatment of a patient who may not have fully developed a condition or disorder, but who is susceptible to, or otherwise at risk of, the condition. Thus, in the claims and embodiments, the methods of the invention can be used either for therapeutic or prophylactic purposes.

Other features and advantages of the invention will be apparent from the following Detailed Description, Examples, Figure, and Claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
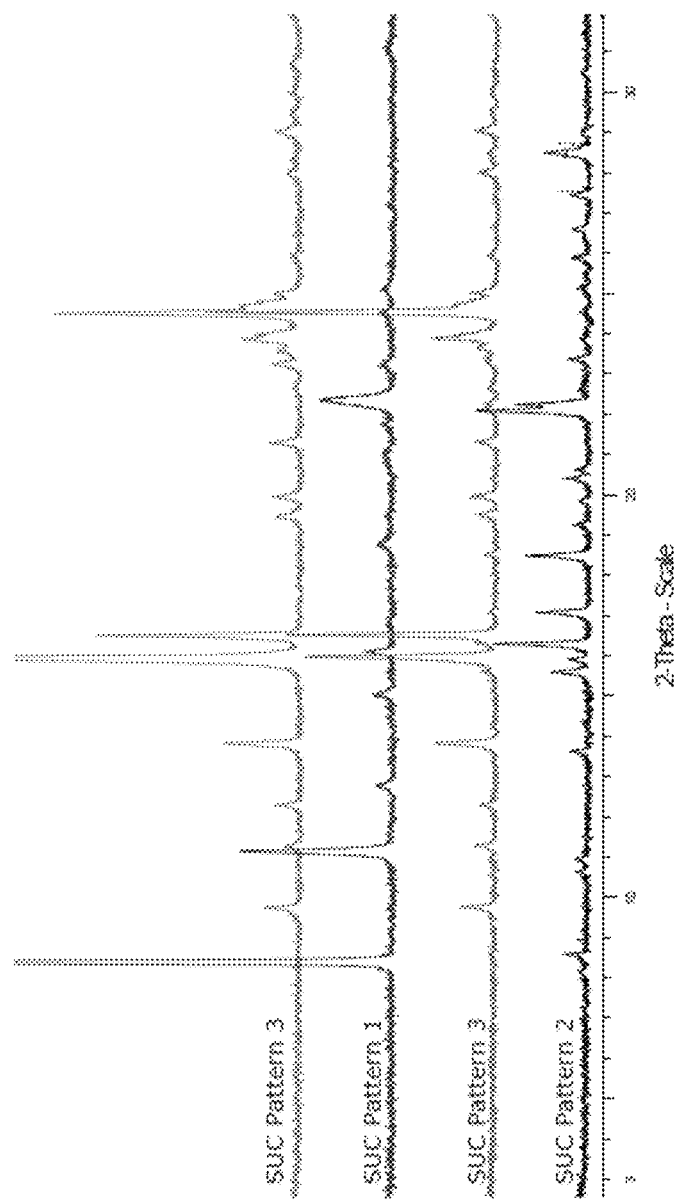
FIG. 1 shows the XRPD patterns of succinic acid psilocin salts having SUC Pattern 1, SUC Pattern 2, or SUC Pattern 3.

To identify psilocin salts with improved properties, a salt screen was performed with 24 different counterions and 3 different solvent systems. Crystalline material with a novel XRPD pattern was isolated from experiments with 13 of the counterions and their properties assessed. Following identification of preferred salts with optimal properties, polymorph screening of these salts was conducted.

Psilocin has the structure:

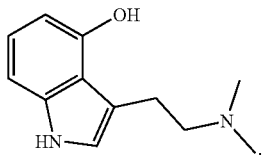

Psilocybin is a phosphate prodrug for psilocin, and when administered to a subject, psilocybin is metabolized to form psilocin. Psilocybin undergoes an enzymatic dephosphorylation reaction resulting in a loss of the phosphate group revealing psilocin's hydroxy group. Psilocybin exists as a zwitterion in which the phosphate and amine ionize each other. The existence of a zwitterion limits the solubility of psilocybin and also curtails its ability to make a salt with an alternate acid that could exist under physiologically tolerated conditions. Removing the phosphate group allows the formation of alternate acid salt forms of psilocin's dimethylamine that are not possible to be prepared with psilocybin. Being able to exist in a non-ionized form, Psilocin is much more lipid soluble in comparison to psilocybin, and therefore is capable of crossing the blood brain barrier more effectively to elicit a response. Psilocin has a high affinity for and is able to activate the 5-HT2A receptor, which plays a key role in regulating mood, sexual behavior, aggression, impulsivity, cognitive function, appetite, pain, sleep, and memory along with other behaviors. As result, psilocin has effects at 5-HT2A receptor that mimic the action of the endogenous neurotransmitter serotonin. This disclosure provides methods for new stable and soluble salt forms of psilocin that are useful in therapy, such as in the treatment of a patient having a psychological condition or a neurological injury.

Treatment Methods

The disclosure provides psilocin salt forms useful for treating psychological conditions, neurological injuries, pain, cephalic pain (e.g., headache), inflammatory conditions, and anxiety.

Psychological Conditions

The psilocin salt forms of the invention can be used to treat psychological conditions. The psychological condition may be any psychological condition described herein. In some embodiments the psychological condition is depression, anxiety, addiction, post-traumatic stress disorder (PTSD), an eating disorder, or compulsive behavior. In some embodiments, the psychological condition may be depression. The psychological condition may also be anxiety. The anxiety may be experienced by a subject who is receiving palliative care or is enrolled in a hospice program. In certain embodiments, the subject who is experiencing anxiety has symptoms such as hypervigilance, fatigue, racing thoughts, irritability, excessive worry, and/or fear.

The subject diagnosed with a psychological condition may be diagnosed by evaluation of the subject's symptoms by a physician, clinician, or therapist based on a physical examination. For example, a blood test may be used to evaluate blood concentration levels of certain biomarkers such as hormones, calcium, vitamin D, electrolytes, and iron in diagnosing depression. Additionally, or alternatively, for patients with a possible depression condition a depression screening test may be performed by the physician, clinician, or therapist to aid in the diagnosis of depression. In some embodiments, the methods described herein may be used to treat psychosomatic pain conditions. In some embodiments, the psychosomatic pain condition may be fibromyalgia, chronic fatigue, migraines, or back pain.

Neurological Injuries

The psilocin salt forms of the invention can be used to treat a neurological injury. The neurological injury may be any neurological injury. In some embodiments, the neurological injury is a stroke, a traumatic brain injury, or a spinal cord injury. The methods of treating a neurological injury described herein may reduce acute inflammation. In certain embodiments, hippocampal hyperactivity is reduced. In particular embodiments, the methods of the invention are used to treat a neurological injury, e.g., stroke, traumatic brain injury, and spinal cord injury, by administering the psilocin salt as needed to pain, inflammation, and/or other symptoms associated with the neurological injury.

Neurodegenerative Conditions

The psilocin salt forms of the invention can be used to treat neurodegenerative conditions. The neurodegenerative condition to be treated can be Alzheimer's disease, Huntington's disease, or Parkinson's disease, among others.

Inflammatory Conditions

The psilocin salt forms of the invention can be used to treat inflammatory conditions. The inflammatory condition to be treated can be a lung inflammation (e.g., chronic obstructive pulmonary disease (COPD)), neuroinflammation (e.g., inflammation associated with Alzheimer's disease), chronic inflammation, rheumatoid arthritis, atherosclerosis, psoriasis, type II diabetes, inflammatory bowel disease, Crohn's disease, multiple sclerosis, and/or septicemia.

Chronic Pain

The psilocin salt forms of the invention can be used to treat conditions associated with chronic pain. The chronic pain may result from post-operative pain, tension headaches, chronic lower back pain, fibromyalgia, nephropathy, multiple sclerosis, shingles, complex regional pain syndrome, cephalic pain, or sciatica. The chronic pain may arise from an operation. The chronic pain may also be pain associated with a particular disease or condition such as nephropathy, multiple sclerosis, shingles, or complex regional pain syndrome. As used herein, a disorder or condition associated with cephalic pain is a disorder or condition which has as one of its symptoms cephalic/head pain (e.g., headache). Examples of such disorders or conditions include trigeminal autonomic cephalalgias such as episodic and chronic cluster headache (CH), episodic and chronic paroxysmal hemicrania (PH), and short-lasting unilateral neuralgiform headache attacks with conjunctival injection and tearing (SUNCT). Other examples of disorders or conditions which can be treated according to the present invention include vascular headaches (e.g., migraine headaches), tension headaches, headaches associated with the use of a substance (e.g., triptans such as sumatriptan, benzodiazepines such as alprazolam, analgesics such as ibuprofen, ergots such as ergotamine, opioids such as morphine, recreational drugs such as caffeine, nicotine, alcohol, and hormone replacement therapy containing, for example, estrogen) or its withdrawal. Yet additional examples of disorders or conditions associated with cephalic pain include miscellaneous headache unassociated with a structural lesion, headache associated with a nonvascular intracranial disorder, headache associated with a non-cephalic infection, headache associated with a metabolic disorder, headache associated with a disorder of the cranium, neck, eyes, nose, sinuses, teeth, mouth, or other facial or cranial structure, nerve trunk pain and deafferentation pain.

Compositions

The invention features pharmaceutical compositions including a psilocin salt form of the invention and a pharmaceutically acceptable excipient. Examples of a pharmaceutically acceptable excipients include, but are not limited to, biocompatible vehicles, adjuvants, additives, and diluents to achieve a composition usable as a dosage form. Examples of other excipients include colloidal silicon oxide, magnesium stearate, cellulose, sodium lauryl sulfate, and D&C Yellow #10.

The pharmaceutical compositions of the invention can include one or more solvents, diluents, or other liquid vehicle, dispersion or suspension aids, surface active agents, isotonic agents, thickening or emulsifying agents, preservatives, solid binders, and lubricants, as suited to the particular dosage form desired. Remington's Pharmaceutical Sciences, Eighteenth Edition, E. W. Martin (Mack Publishing Co., Easton, Pa., 1990) discloses various excipients used in formulating pharmaceutical compositions and known techniques for the preparation thereof. Except insofar as any conventional excipient medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable excipients include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; natural and synthetic phospholipids, such as soybean and egg yolk phosphatides, lecithin, hydrogenated soy lecithin, dimyristoyl lecithin, dipalmitoyl lecithin, distearoyl lecithin, dioleoyl lecithin, hydroxylated lecithin, lysophosphatidylcholine, cardiolipin, sphingomyelin, phosphatidylcholine, phosphatidyl ethanolamine, diastearoyl phosphatidylethanolamine (DSPE) and its pegylated esters, such as DSPE-PEG750 and, DSPE-PEG2000, phosphatidic acid, phosphatidyl glycerol and phosphatidyl serine; and hydroxypropyl-beta-cyclodextrin and sulfonic acid substituted cyclodextrin (e.g., CAPTISOL™). Commercial grades of lecithin which are preferred include those which are available under the trade name Phosal® or Phospholipon® and include Phosal 53 MCT, Phosal 50 PG, Phosal 75 SA, Phospholipon 90H, Phospholipon 90G and Phospholipon 90 NG; soy-phosphatidylcholine (SoyPC) and DSPE-PEG2000 are particularly preferred; buffering agents such as magnesium hydroxide and aluminum hydroxide; alginic acid; pyrogen-free water; isotonic saline; Ringer's solution; 5% dextrose solution and combinations with the foregoing aqueous solutions; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The above-described compositions, in any of the forms described above, can be used for treating a disease or condition described herein. An effective amount refers to the amount of an active compound/agent that is required to confer a therapeutic effect on a treated subject. Effective doses will vary, as recognized by those skilled in the art, depending on the types of diseases treated, route of administration, excipient usage, and the possibility of co-usage with other therapeutic treatment. A pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

For use in the methods and compositions of the invention, the pharmaceutically acceptable psilocin salt, may be contained in any appropriate amount in any suitable carrier substance formulated for intravenous infusion and is generally present in an amount of 0.01-95% by weight of the total weight of the composition. In particular embodiments, the pharmaceutically acceptable psilocin salt is present in an amount of 0.01-5% by weight of the of the total weight of the composition. In some embodiments, an aqueous solution suitable for intravenous infusion including the pharmaceutically acceptable psilocin salt may be formulated in a saline solution. The formulation of infusions is well known to those skilled in the art of pharmaceutical formulation. Formulations can be found in Remington: The Science and Practice of Pharmacy ($23^{rd}$ ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Compositions for infusion use may be provided in unit dosage forms (e.g., in single-dose ampoules), or in vials containing several doses and in which a suitable preservative may be added. The solution of the pharmaceutically acceptable psilocin salt suitable for intravenous infusion may have a pH of about 3 and about 9 (e.g., 3±1, 4±1, 5±1, 6±1, 7±1, 8±1, and 9±1). Furthermore, the solution of the pharmaceutically acceptable psilocin salt suitable for intravenous infusion may include a concentration of the pharmaceutically acceptable psilocin salt between about 0.1 mg/mL and about 50 mg/mL (e.g., 0.1±0.1 mg/mL, 0.2±0.1 mg/mL, 0.3±0.1 mg/mL, 0.4±0.1 mg/mL, 0.5±0.5 mg/mL, 1±0.5 mg/mL, 2±1 mg/mL, 3±1 mg/mL, 4±1 mg/mL, 5±1 mg/mL, 6±1 mg/mL, 7±1 mg/mL, 8±1 mg/mL, 9±1 mg/mL, 10±1 mg/mL, 11±1 mg/mL, 12±1 mg/mL, 13±1 mg/mL, 14±1 mg/mL, 15±1 mg/mL, 16±1 mg/mL, 17±1 mg/mL, 18±1 mg/mL, 19±1 mg/mL, 25±5 mg/mL, 30±5 mg/mL, 35±5 mg/mL, 40±5 mg/mL, 45±5 mg/mL, and 50±5 mg/mL). In some embodiments, the aqueous solution has between about 1 mg/mL and about 15 mg/mL (e.g., 1±1 mg/mL, 2±1 mg/mL, 3±1 mg/mL, 4±1 mg/mL, 5±1 mg/mL, 6±1 mg/mL, 7±1 mg/mL, 8±1 mg/mL, 9±1 mg/mL, 10±1 mg/mL, 11±1 mg/mL, 12±1 mg/mL, 13±1 mg/mL, 14±1 mg/mL, and 15±1 mg/mL) of any one of pharmaceutically acceptable salts of psilocin described herein. In particular embodiments, the aqueous solution has between about 0.1 mg/mL and about 1 mg/mL (e.g., 0.1±0.1 mg/mL, 0.2±0.1 mg/mL, 0.3±0.1 mg/mL, 0.4±0.1 mg/mL, 0.5±0.1 mg/mL, 0.6±0.1 mg/mL, 0.7±0.1 mg/mL, 0.8±0.1 mg/mL, 0.9±0.1 mg/mL, and 1±0.1 mg/mL) of any one of pharmaceutically acceptable salts of psilocin described herein.

A sterile injectable composition can be a solution or suspension in a non-toxic parenterally acceptable diluent or solvent. Such solutions include, but are not limited to, 1,3-butanediol, mannitol, water, Ringer's solution, and isotonic sodium chloride solution. In addition, fixed oils are conventionally employed as a solvent or suspending medium (e.g., synthetic mono- or diglycerides). Fatty acids, such as, but not limited to, oleic acid and its glyceride derivatives, are useful in the preparation of injectables, as are natural pharmaceutically acceptable oils, such as, but not limited to, olive oil or castor oil, or polyoxyethylated versions thereof. These oil solutions or suspensions also can contain a long chain alcohol diluent or dispersant such as, but not limited to, carboxymethyl cellulose, or similar dispersing agents. Other commonly used surfactants, such as, but not limited to, Tweens or Spans or other similar emulsifying agents or bioavailability enhancers, which are commonly used in the manufacture of pharmaceutically acceptable solid, liquid, or other dosage forms also can be used for the purpose of formulation.

A composition for oral administration can be any orally acceptable dosage form including capsules, tablets, emulsions and aqueous suspensions, dispersions, and solutions. In the case of tablets, commonly used excipients include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The above-described compositions, in any of the forms described above, may be stored in a light impenetrable container. For the example, the compositions described herein may be contained in an amber bottle.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1. Salt Screens

In three solvent systems, dissolved psilocin was separately combined with 24 organic and inorganic acids, see Table 1.

TABLE 1

List of acids used in psilocin salt screen

| # | Acid |
|---|---|
| 1 | Hydrobromic acid |
| 2 | Hydrochloric acid |
| 3 | 1-5-Naphthalene disulphonic acid |
| 4 | Sulphuric acid |
| 5 | p-Toluene sulphonic acid |
| 6 | Methane sulphonic acid |
| 7 | Oxalic acid |
| 8 | Maleic acid |
| 9 | Phosphoric acid |
| 10 | Ketoglutaric acid |
| 11 | L-Tartaric acid |

TABLE 1-continued

List of acids used in psilocin salt screen

| # | Acid |
|---|---|
| 12 | Fumaric acid |
| 13 | Citric acid |
| 14 | L-Malic acid |
| 15 | D-Gluconic acid, 50% in water |
| 16 | Benzoic acid |
| 17 | Succinic acid |
| 18 | Acetic acid |
| 19 | Nicotinic acid |
| 20 | Propionic acid |
| 21 | Pamoic Acid |
| 22 | Adipic Acid |
| 23 | Oleic Acid |
| 24 | Salicylic Acid |

Some combinations did not afford a solid product even after cooling or counter solvent addition. Other combinations produced crystals which were analyzed by X-Ray Powder Diffraction (XPRD). XRPD diffractograms were collected on a Bruker D8 diffractometer using Cu Kα radiation (λ=1.54° A, 40 kV, 40 mA) and a θ-2θgoniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions as flat plate specimens using powder as received. The sample was prepared on a polished, zero-background (510) silicon wafer by gently pressing onto the flat surface or packed into a cut cavity. The sample was rotated in its own plane. The details of the standard data collection methods are: (i) angular range: 2 to 42° 2θ; (ii) step size: 0.05° 2θ; and (iii) collection time: 0.5 s/step (total collection time: 6.40 min).

Crystalline material with a novel XRPD pattern was isolated from experiments with 13 of the counterions and their properties assessed. Psilocin acetate (ACE) Pattern 2, psilocin adipate (ADI) Pattern 1, ADI Pattern 2, psilocin fumarate (FUM) Pattern 1, FUM Pattern 2, psilocin 1,5-napthalenedisulfonate (NAP Pattern 2), psilocin oxalate (OX) Pattern 1, OX Pattern 2, psilocin phosphonate (PHO) Pattern 1, PHO Pattern 2, psilocin propionate (PRO) Pattern 1, psilocin succinate (SUC) Pattern 1, SUC Pattern 2, psilocin salicylate (SAL) Pattern 1, SAL Pattern 2 were shown to convert or partially convert to a new XRPD pattern after storage at 40° C./75% relative humidity for 7 days, indicating that these salt forms are not stable. For this reason, these patterns were dismissed. The thermal data for psilocin pamoate (PAM) Pattern 1 showed large mass losses in the TGA and a number of endothermic events in the DSC, making it undesirable to take forward. A limited number of combinations did provide a solid product, which were evaluated further for stability (HPLC), crystallinity (XRPD), and counter ion stoichiometry (NMR) and polymorphic forms and stability (XRPD). From this screening only three psilocin/acid combinations were deemed worthy of scale up and more detailed evaluation.

Screens of various psilocin salts were completed in acetone, 2-methyltetrahydrofuran and ethanol:$H_2O$ (9:1) generating 22 crystalline forms which were characterized using X-ray Powder Diffraction (XRPD), high pressure liquid chromatography (HPLC), $^1$H-NMR, Thermogravimetric analysis/Differential scanning calorimetry (TGA/DSC), and were also assessed after static storage for 7 days at 40° C. and 75% relative humidity using XRPD and HPLC, the results of which are summarized in Table 2. The samples that were stored at 40° C. and 75% relative humidity were denoted with the numbers 40-75 after the sample number. Solid state stability, enhancement of purity upon crystallization, minimum polymorphic forms, lack of hydrates, alcoholates or solvent inclusion as well as solubility of the salt in physiological saline were identified as a key parameters for selection of the most preferred salt forms; as such, small scale-up experiments on 7 salts were carried out to allow for the collection of solubility data, see Example 2.

The salt screen was performed by adding the appropriate counterion, either as a solution or as a solid, to a solution of psilocin free base in the appropriate solvent system at room temperature. This was then stirred at room temperature for 1 hour before cooling to 5° C. and stirring at 5° C. overnight. If a solid was isolated at this point, then in was separated by filtration. If a solution or gum was isolated at this point, further treatment was carried out as required by addition of a further 0.5 molar equivalents of the counterion, temperature cycling between 5 and 25° C., and/or addition of an antisolvent.

TABLE 2

Characteristics of Isolated Solids of Psilocin Salts

Figure 2:
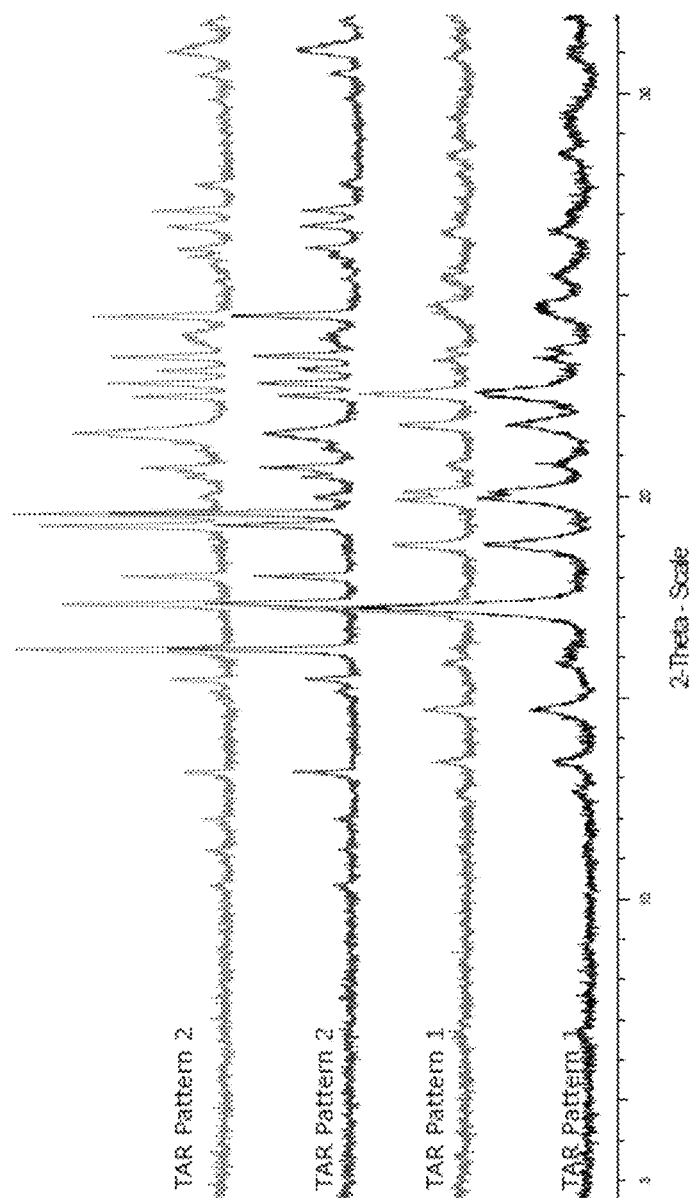
FIG. 2 shows the XRPD patterns of L-tartaric acid psilocin salts having TAR Pattern 1 or TAR Pattern 2.
Figure 3:
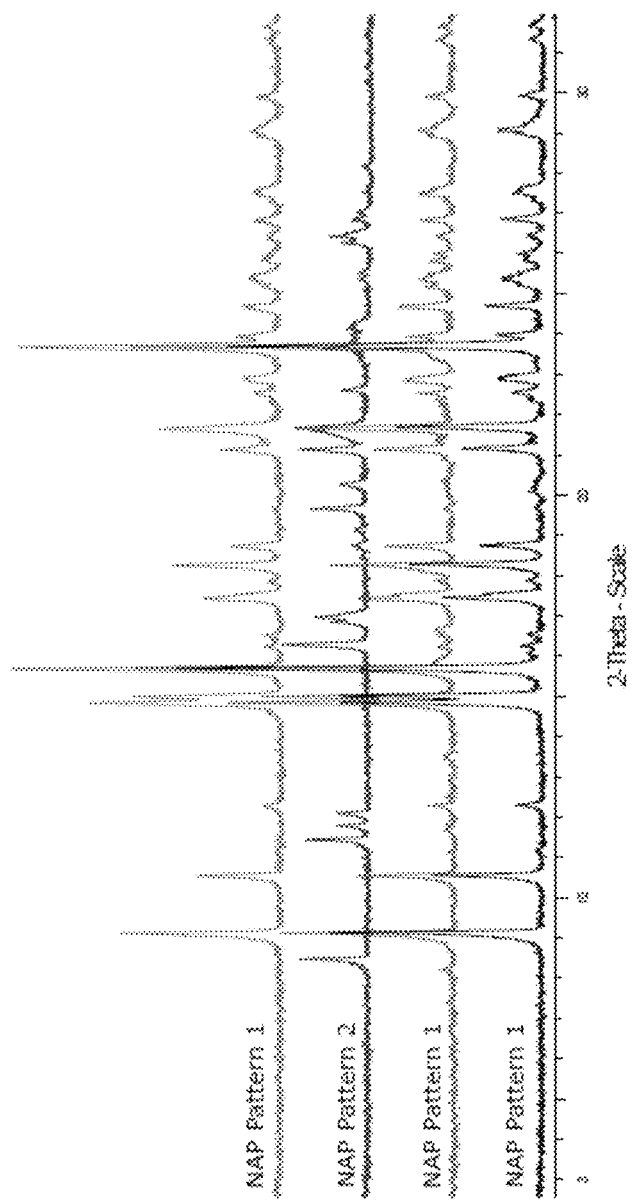
FIG. 3 shows the XRPD patterns of 1,5-naphthalenedisulfonic acid psilocin salts having NAP Pattern 1 or NAP Pattern 2.

| Sample | XRPD | HPLC | $^1$H-NMR | Thermal (TGA/DSC) | Static Storage 40° C./75% RH |
|---|---|---|---|---|---|
| Psilocin succinate | SUC Pattern 1 (FIG. 1) | 99.5% | 0.5 mole eq. of succinate, i.e., dicarboxylate. 0.16 mole eq. of acetone. | 0.8% mass loss from 40-85° C. A second mass loss event from 85-115° C. equating to 6.6% mass lost. This event is concurrent with an endotherm in the DSC, onset 93.8° C. (26 J/g). Large sharp endotherm, onset 183.5° C. (125 J/g) 7.4% mass loss may be 0.16 mol eq. acetone and 0.65 mole eq. water | XRPD- SUC Pattern 3 HPLC-99.3% |
| Psilocin acetate | ACE Pattern 1 | 98.5% | Poor spectrum (not enough sample). Ca. 1 mol eq. of acetic acid. Ca. 0.3 mol eq. of acetone. Extra peak at 6.51 ppm. | Insufficient Sample | XRPD- ACE Pattern 1 + extra peaks (small amount of sample). HPLC-75.2% |
| Psilocin phosphate | PHO Pattern 1 (poorly crystalline) | 96.9% | Consistent with structure. 0.17 mol eq. of 2-MeTHF. | Gradual mass loss of 10.8% from 45-200° C. DSC contains a number of endotherms, onset 74.7° C. (2 J/g), broad event between 105-140° C. (32 J/g). There are two sharp endotherms at 100° C. and 206° C. that resemble artifacts. (small sample size) 10.8% mass loss = 0.17 mol eq. 2-MeTHF and 1.22 mol eq. of water | XRPD- PHO Pattern 2 (possible preferred orientation) HPLC- 93.9% |
| Psilocin tartrate | TAR Pattern 1 (FIG. 2) | 98.5% | 1.07 mol eq. of tartrate. 0.17 mol eq. 2-MeTHF and possibly 0.09 mol eq. of THF | 0.6% mass loss between 30-95° C.. An additional 4.4% is lost from 95-160° C. and is followed by a endotherm in the DSC, onset 161.9° C. (90 J/g). 5.0% mass loss may be loss of 0.17 mol eq. 2-MeTHF and 0.06 mol eq. THF | XRPD- TAR Pattern 1 HPLC-96.3% |
| Psilocin 1,5-napthalene disulfonate | NAP Pattern 2 (FIG. 3) | 99.4% | Consistent with structure (one psilocin CH$_2$ signal possibly overlapping with water peak). 0.5 mol eq. of counterion. 0.73 mol eq. ethanol. | 0.8% mass lost between 25-75° C. and a second event between 75-110° C. equating to 7.1% mass lost. Endotherm in the DSC, onset 82.4° C. (73 J/g). Endotherm onset 124.3° C. (17 J/g). Small broad endotherm, onset 197.1° C. (2 J/g). Finally, there is a large sharp endotherm with an onset at 252.7° C. (72 J/g). 7.9% mass loss may be loss of 0.73 mol eq. ethanol and, 0.48 mol eq. water. | XRPD- NAP Pattern 1 (FIG. 3) HPLC-99.2% |
| Psilocin tartrate | TAR Pattern 2 (FIG. 2, second scan from top) | 97.9% | Consistent with structure. 1.1 mol eq. of tartrate. 0.03 mole eq. ethanol | Mass loss of 4.1% from 40-95° C. accompanied by a broad endotherm in the DSC, onset 41.2° C. (85 J/g). There is a small endotherm at 125.6° C. (9 J/g) and a large sharp endotherm at 165.9° C. (72 J/g). 4.1% mass loss may be loss of 0.84 mol eq. of water | XRPD- TAR Pattern 2 (FIG. 2) HPLC-98.0% |
| Psilocin oxalate | OX Pattern 1 | 96.8% | 0.3 mol eq. Acetone. 0.1 mol eq. THF. 0.7 mole eq. oxalate by IC | Insufficient Sample | XRPD OX Pattern 3 HPLC-94.4% |
| Psilocin oxalate | OX Pattern 2 | 95.5% | 0.26 mol eq. 2-MeTHF. 0.95 mole eq. oxalate by IC. | 8.4% mass loss over two events. May be loss of 2-MeTHF and water. A number of events in DSC. | XRPD- OX Pattern 3 + extra peaks HPLC-97.1% |

TABLE 2-continued

Characteristics of Isolated Solids of Psilocin Salts

| Sample | XRPD | HPLC | ¹H-NMR | Thermal (TGA/DSC) | Static Storage 40° C./75% RH |
|---|---|---|---|---|---|
| Psilocin tartrate | TAR Pattern 1 + TAR Pattern 2 | 96.4% | 1.1 mol eq. of tartrate. 0.03 mole eq. ethanol | 1.2% mass loss between room temperature and 170° C.. Small endotherm 125° C. (2 J/g). Sharp endotherm onset 150° C. | XRPD- TAR Pattern 1 + TAR Pattern 2 HPLC- 97.0% |
| Psilocin fumarate | FUM Pattern 1 | 98.9% | 0.5 mol eq. fumarate. 0.26 mol eq. acetone | 8.3% mass loss between 100 and 140° C., Endotherm onset 119.9° C. (69 J/g). | XRPD- FUM Pattern 3 HPLC- 99.3% |
| Psilocin fumarate | FUM Pattern 1 | 98.3% | 0.5 mol eq. of fumarate. 0.52 mol eq. of 2-MeTHF. | 13.2% mass loss from 80-165° C. which may be loss of 2-MeTHF | XRPD- FUM Pattern 4 HPLC- 98.3% |
| Psilocin benzoate | BEN Pattern 1 | 98.8% | 1 mol eq. of benzoate. 0.03 mol eq. of acetone | 1.0% mass loss 125-180° C.. Small endotherm, onset 126.4° C. (9 J/g). | XRPD- BEN Pattern 1 HPLC- 99.0% |
| Psilocin succinate | SUC Pattern 2 (FIG. 1) | 98.7% | 0.5 mol eq. of succinate (dicarboxylate). 0.46 mol eq. of 2-MeTHF. | 13.7% mass loss over two events. Number of events in DSC | XRPD- SUC Pattern 3 HPLC- 98.8% |
| Psilocin propionate | PRO Pattern 1 | 99.4% | 1 mol eq. propionate | Insufficient Sample | XRPD- PRO Pattern 1 + very small amount of PRO Pattern 3 HPLC-99.4% |
| Psilocin pamoate | PAM Pattern 1 | 99.2% | 1 mol eq. pamoate. 2.5 mol eq. of DMSO | 15.8% mass loss from 25-140° C. 17.8% mass loss from 150-260° C.. Both with associated endotherms in the DSC. | XRPD- PAM Pattern 1 HPLC- 99.6% |
| Psilocin adipate | ADI Pattern 1 | 98.6% | 0.55 mol eq. of adipate. 0.32 mol eq. of THF. 0.07 mol eq. of acetone | 4.5% mass loss from 70-125° C. 4.7% mass loss from 145-180° C. Decomp onset at ca. 215° C. A number of endothermic events in DSC. | XRPD- ADI Pattern 1 + extra peaks. HPLC- 98.4% |
| Psilocin adipate | ADI Pattern 2 | 98.1% | 0.54 mol eq. of adipate. 0.27 mol eq. 2-MeTHF. 0.17 mol eq. THF. | 10.1% mass loss attributed to the THF and 2-MeTHF. A number of endothermic events in DSC. | XRPD- ADI Pattern 3 HPLC-98.1% |
| Psilocin salicylate | SAL Pattern 1 | 98.9% | 1 mol eq. of salicylic acid. 0.01 mol eq. of acetone. | 1.5% mass loss from 110-185° C., leading into degradation. The DSC contains three endotherms. Onsets at 124.4° C., 153.7° C. and 178.5° C. with energies of 27 J/g, 24 J/g, and 64 J/g respectively. | XRPD- SAL Pattern 1 + extra peak (21.5°) HPLC-99.1% |
| Psilocin salicylate | SAL Pattern 2 | 99.4% | 0.87 mol eq. salicylate. | No mass loss until degradation | XRPD- SAL Pattern 2 + extra peak 21.5° HPLC- 99.8% |
| Psilocin 1,5-napthalene disulfonate | NAP Pattern 1 (FIG. 3) | 97.2% | Consistent with structure. 0.6 mole eq. of counterion | Total 2.4% mass loss, 0.5 mol eq. water. A number of endothermic events in DSC. | XRPD- NAP Pattern 1 HPLC-97.2% |
| Psilocin acetate | ACE Pattern 2 | 98.8% | 1 mol eq. of acetate | Insufficient Sample | XRPD- ACE Pattern 3 HPLC-83.4% |

The psilocin benzoate, psilocin succinate, and psilocin tartrate salts were all investigated in their anhydrous forms.

The psilocin benzoate salt having the BEN Pattern 1 exhibited the lowest solubility and intrinsic dissolution rate (IDR) of the three forms but was still significant and pharmaceutically consistent. The psilocin benzoate salt having the BEN Pattern 1 also had a substantial increase with respect to solubility and IDR over the free base form. The psilocin benzoate having the BEN Pattern 1 was shown to be stable, exhibited no polymorphism, and was non-hygroscopic (Table 3).

The psilocin succinate salt having the SUC Pattern 3 had the highest IDR as well as high solubility. This form was a hemi-salt and was stable to static storage. The material was hygroscopic (2.1% reversible mass change between 0-90% RH), however, this did not appear to result in a change of form and most of the water uptake occurred between 80% and 90% RH.

The psilocin tartrate salt having the TAR Pattern 1 contained some residual solvent which was removed by storage at 40° C./75% RH. It had a high solubility and the second highest IDR. It converted to TAR Pattern 3 under storage at 25° C./97%.

A summary of the characteristics of the psilocin salts is provided in Table 4.

TABLE 3

Stability of Psilocin Salts over time

| Static Storage 40° C./75% RH | As Synthesized | 1 Weeks | 3 Weeks |
|---|---|---|---|
| TAR Pattern 1 | 97.2% | 96.6% | 96.6% |
| SUC Pattern 3 | 99.3% | 98.8% | 96.2% (material is brown) |
| BEN Pattern 1 | 99.3% | 99.3% | 99.3% |

| Static Storage 25° C./97% RH | As Synthesized | 1 Weeks | 3 Weeks |
|---|---|---|---|
| TAR Pattern 1 | 97.2% | 96.7% (form changed to TAR Pattern 3) | 95.9% (form changed to TAR Pattern 3) |
| SUC Pattern 3 | 99.3% | 98.7% | 91.7% (material is brown) |
| BEN Pattern 1 | 99.3% | 99.3% | 99.3% |

Example 2. 100 mg Scale Up for Solubility Assessment

Procedures were adapted from the small scale screen from which each target solid was obtained and characterized using XRPD, $^1$H-NMR, and HPLC as shown in Table 5. The solvents used were purged with $N_2$ for at least 30 minutes prior to use. Obtained solids were dried in a vacuum oven at room temperature for 2 hours.

Psilocin salicylate was made by combining a 100 mg of psilocin free base in a 4 mL vial with 30 volumes of acetone at 25° C. To this solution, 1.1 molar equivalents of salicylic acid (1M in THF) was added. The crystallization was performed by cooling the solution to 5° C. at a rate of 0.25° C./min and held 5° C. for 2 hours at which point an additional 0.5 mole equivalents of salicylic acid was added. The crystallization solution was held at 5° C. for another 10 hours, after which, 10 volumes of heptane were added to the clear solution and stirring was continued for a further 24 hours. The white suspension was isolated using positive pressure using a fritted filter cartridge and resulted in a yield of 86.38 mg.

Psilocin succinate was made by combining 100 mg of psilocin free base in a 4 mL vial and with 30 volumes of acetone at 25° C. To this solution, 1.1 molar equivalents of succinic acid (1M in methanol) was added. The crystalliza-

TABLE 4

Summary Characterization of Psilocin Salts

| Characterization | TAR Pattern 1 | SUC Pattern 3 | BEN Pattern 1 |
|---|---|---|---|
| Polymorphism | 4 Observed Patterns | 5 Observed Patterns | 1 Observed patter |
| Solubility in Saline | 64 mg/mL | >27 mg/mL | 5.0 mg/mL |
| IDR (mg/min/cm2) [Freeform = 0.09] | 6.9 | 12.4 | 0.4 |
| $^1$H-NMR | 1 mole equivalent of tartrate. 0.1 mole equivalents of residual 2-MeTHF and ca.0.02 of THF. | 0.5 mole equivalents of succinate. <0.01 mole equivalents of acetone | 1 mole equivalents of benzoate. 0.07 mole equivalents of 2-MeTHF and 0.015 mole equivalents of IPA |
| Thermal Data | 2.4% mass loss between 110-165° C. attributed to loss of trapped solvent upon melting of the material, decomposition onset after 165° C.. (0.1 mole equivalent of 2-MeTHF = 2.4% mass loss). Large melt endotherm, onset 162.3° C. (103 J/g) | No mass loss until decomposition. sharp endotherm, onset 186.9° C. (123 J/) | No mass loss until Large decomposition, starting from 200° C.. DSC contains one large endotherm, onset 238.4° C. (178 J/g), likely melt based on HSM data |
| GVS | Reversible 1.4% mass change between 0-90% RH with no hysteresis. Slightly Hygroscopic | A reversible 2.1% mass change between 0 90% RH with no hysteresis. Only 1.0 % mass change between 0 and 80% RH. | Reversible 0.25% mass change between 0-90% RH. Non-hygroscopic. |
| HPLC Purity Static Storage | 97.2% Converted to TAR Pattern 3 at 25° C., 97% RH. Slight drop in purity at 25° C./ 97% RH. | 99.3% Form is stable. HPLC shows substantial drop in purity after 3 weeks, particularly at 25° C./97% RH | 99.3% Form is stable. No drop in purity. |
| Further Comments | Residual solvent can be removed by storage at 40° C., 75% RH with some water being picked up as well. | | Small endotherm seen in DSC on initial analysis is no longer present. | tion was performed by cooling the solution to 5° C. at a rate of 0.25° C./min and holding at this temperature for 12 hours. The white suspension was isolated using positive pressure using a fritted filter cartridge and resulted in a yield of 89.96 mg.

Psilocin tartrate was made by combining 100 mg of psilocin free base in a 4 mL vial with 30 volumes of 2-methyltetrahydrofuran at 25° C. To this solution, 1.1 molar equivalents of L-tartaric acid (1M in THF) was added. The crystallization was performed by cooling the solution to 5° C. at a rate of 0.25° C./min and holding at this temperature for 12 hours. The off-white suspension was isolated using positive pressure using a fritted filter cartridge and resulted in a yield of 160.30 mg Psilocin 1,5-napthalenedisulfonate was made by combining 100 mg of psilocin free base in a 4 mL vial with 30 volumes of 2-methyltetrahydrofuran at 25° C. To this solution, 1.1 molar equivalents of 1,5-naphthalenedisulfonic acid (1M in THF) was added. The crystallization was performed by cooling the solution to 5° C. at a rate of 0.25° C./min and holding at this temperature for 12 hours. The white suspension was isolated using positive pressure using a fritted filter cartridge and resulted in a yield of 154.37 mg.

Psilocin salicylate was made by combining 100 mg of psilocin free base in a 4 mL vial with 30 volumes of 2-methyltetrahydrofuran at 25° C. To this solution, 1.1 molar equivalents of salicylic acid (1M in THF) was added. The crystallization was performed by cooling the solution to 5° C. at a rate of 0.25° C./min, after which crystallization had occurred so no further salicylic acid was added. The crystallization was held further at 5° C. for 12 hours. The white suspension was isolated using positive pressure using a fritted filter cartridge and resulted in a yield of 101.99 mg.

Psilocin benzoate was made by combining 100 mg of psilocin free base in a 20 mL vial with 30 volumes of 2-methylhydrofuran at 25° C. To this solution, 1.1 molar equivalents of benzoic acid (0.5M in isopropyl alcohol) was added. The crystallization was then performed by cooling the solution to 5° C. at 0.25° C./min and holding at this temperature for 12 hours. The white suspension was isolated using positive pressure using a fritted filter cartridge and resulted in a yield of 135.81 mg.

Psilocin tartrate was made by combining 100 mg psilocin free base in a 20 mL vial with 40 volumes of EtOH:water (9:1) at 25° C. To this solution, 1.1 molar equivalents of L-tartaric acid (1M in tetrahydrofuran). The crystallization was performed by cooling the solution to 5° C. at a rate of 0.25° C./min and holding at this temperature for 12 hours. The white suspension was isolated using positive pressure using a fritted filter cartridge and resulted in a yield of 103.67 mg.

Psilocin hydrochloride was made by combining 100 mg of psilocin free base in a 20 mL vial with 40 volumes of acetonitrile at 25° C. To this solution, 1.1 molar equivalents of hydrochloride (1M in tetrahydrofuran) was added. The crystallization was performed by cooling the solution to 5° C. at a rate of 0.25° C./min at which point 10 volumes of methyl tert-butyl ether was added and the reaction was stirred for a further 12 hours at 5° C. There was only a small amount of brown material on vial wall so a further 5 volumes of methyl tert-butyl ether were added and the crystallization solution and stirred at 5° C. for 72 hours. The off-white material crystallized on the vial-solvent interface and was knocked off before being isolated using positive pressure using a fritted filter cartridge and resulted in a yield of 32.51 mg.

A second crop of light tan material was obtained by adding 25 volumes of methyl tert-butyl ether, a small amount of seed material, and 0.55 molar equivalents of hydrochloride (1M in tetrahydrofuran) and stirred at 5° C. for 72 hours and resulted in a yield of 20-30 mg. The results of which are summarized in Table 6.

TABLE 5

Figure 4:
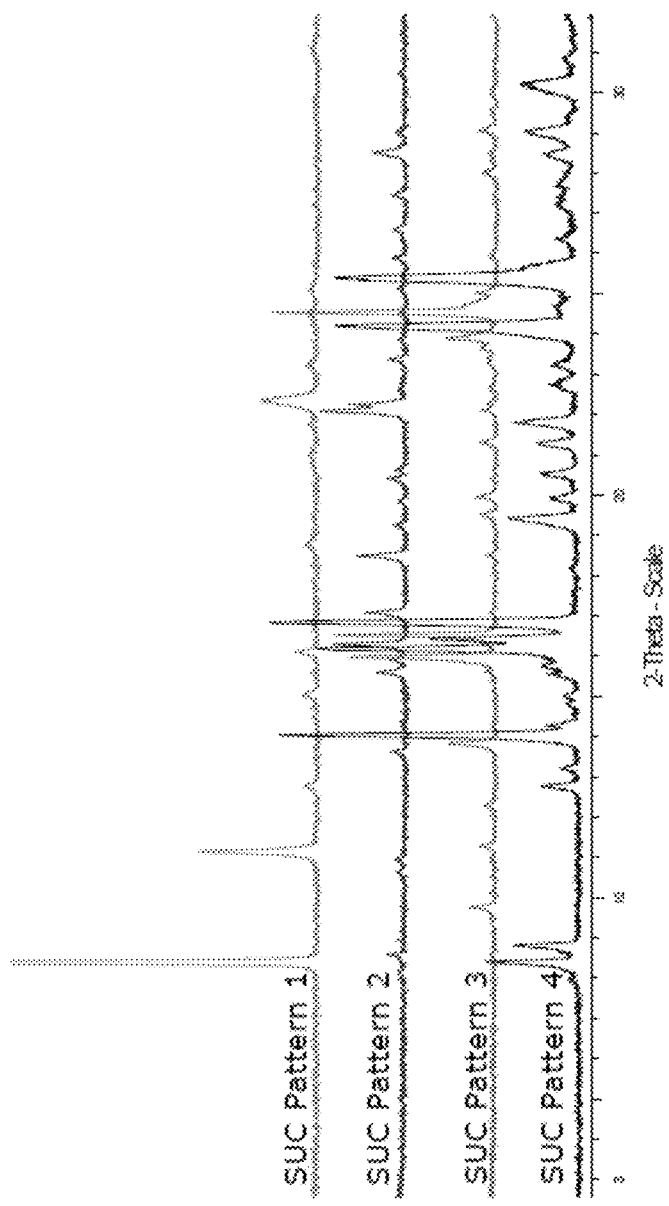
FIG. 4 shows the XRPD pattern of psilocin succinate having SUC Pattern 4 (bottom scan).
Figure 6:
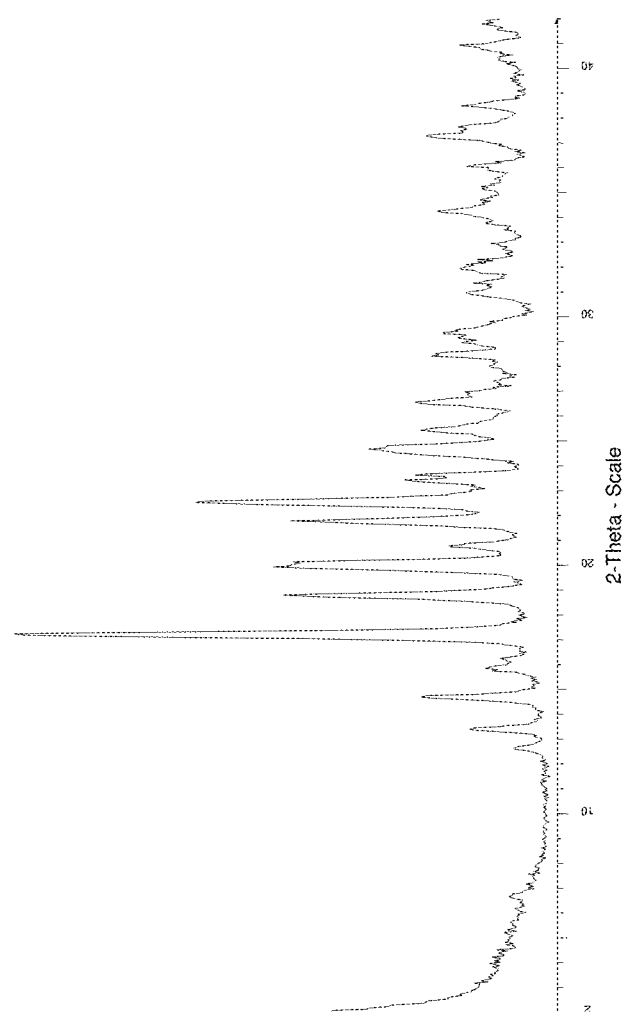
FIG. 6 shows the XRPD of the TAR Pattern 1 from psilocin tartrate crystalline solid.
Figure 7:
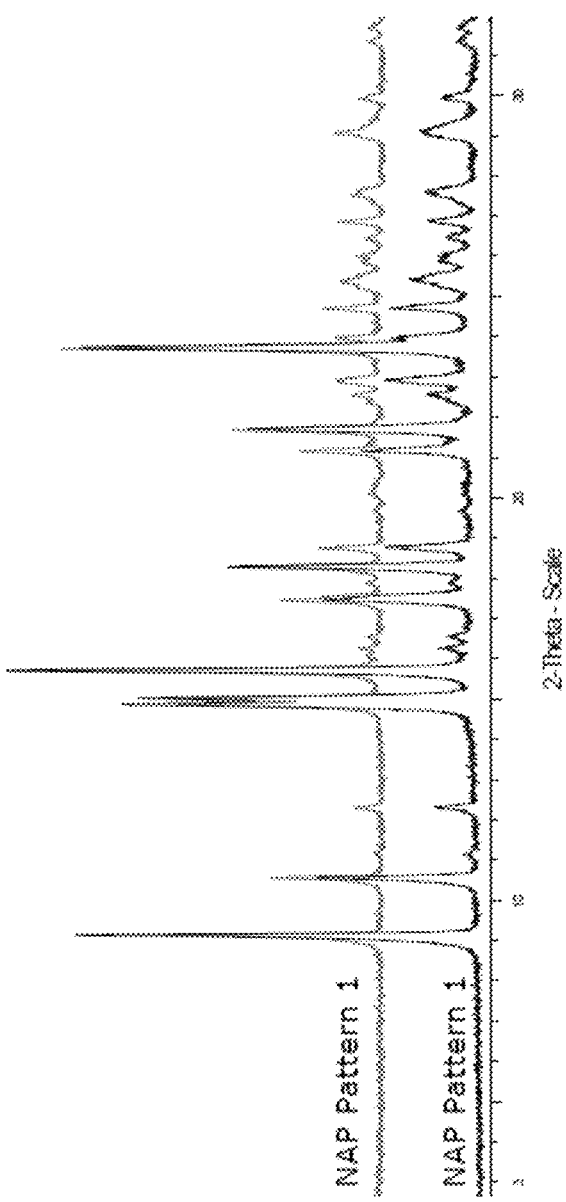
FIG. 7 shows the XRPD pattern of NAP Pattern 1 from psilocin 1,5-naphthalenedisulfonate (bottom scan).
Figure 8:
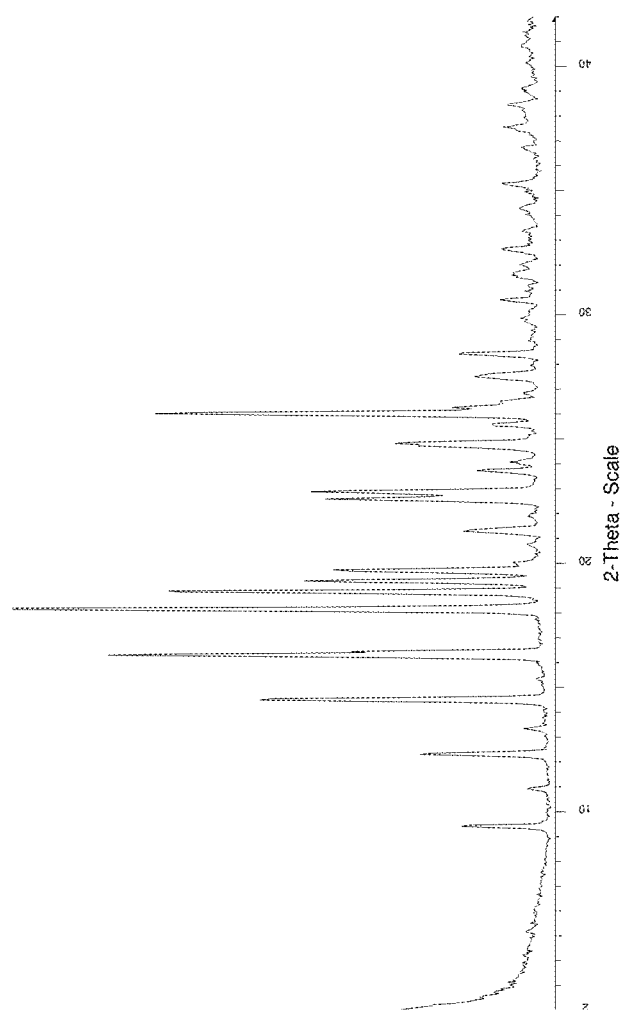
FIG. 8 shows the XRPD of the BEN Pattern 1 from psilocin benzoate crystalline solid.

| Salt characterization of psilocin salts after 100 mg scale up | | | | |
|---|---|---|---|---|
| Salt | Target | XRPD | $^1$H-NMR | HPLC Purity |
| Psilocin salicylate | SAL Pattern 1 | SAL Pattern 1*** | Consistent with structure. 1 mol eq. salicylic acid. 0.02 mol eq. acetone | 99.2% |
| Psilocin succinate | SUC Pattern 1 | SUC Pattern 4** (FIG. 4) | Consistent with structure. 0.5 mol eq. of succinate. 0.41 mol eq. of acetone | 99.1% |
| Psilocin tartrate | TAR Pattern 1 | TAR Pattern 1*** (FIG. 6) | Consistent with structure. 1 mol eq. L-tartrate. 0.04 mol eq. 2-MeTHF | 96.7% |
| Psilocin 1,5-napthalenedisulfonate | NAP Pattern 1 | NAP Pattern 1*** (FIG. 7) | Consistent with structure. 0.7 mol eq. of counter ion. 0.12 mol eq. 2-MeTHF. | 97.4% |
| Psilocin salicylate | SAL Pattern 2 | SAL Pattern 1* | Consistent with structure. 1 mol eq. salicylic acid. | 99.0% |
| Psilocin benzoate | BEN Pattern 1 | BEN Pattern 1*** (FIG. 8) | Consistent with structure. 1 mol eq. benzoic acid. 0.07 and 0.02 mol eq. 2-MeTHF and IPA respectively | 99.4% |

TABLE 5-continued

Salt characterization of psilocin salts after 100 mg scale up

Figure 9:
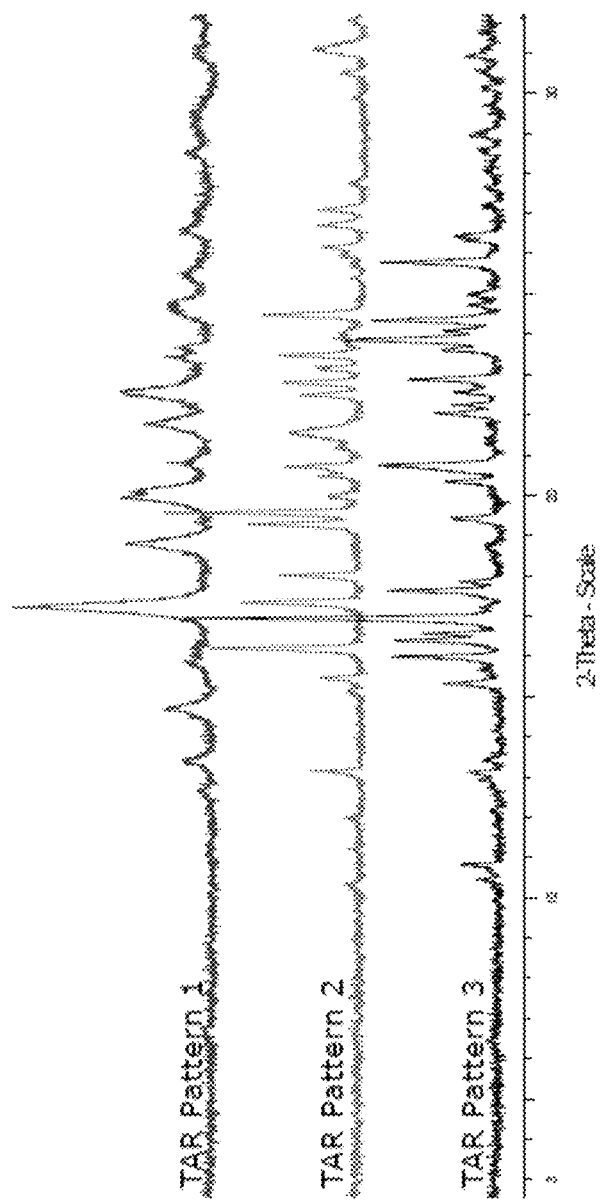
FIG. 9 shows the XRPD pattern of TAR Pattern 3 from psilocin tartrate (bottom scan).

| Salt | Target | XRPD | ¹H-NMR | HPLC Purity |
|---|---|---|---|---|
| Psilocin tartrate | TAR Pattern 2 | TAR Pattern 3** (FIG. 9) | Consistent with structure. 1 mol eq. of tartrate. 0.03 mol eq. of ethanol | 98.3% |

*Previously characterized form
**Uncharacterized form
***Target form crystallized

TABLE 6

Characterization of psilocin salt solids

Figure 5:
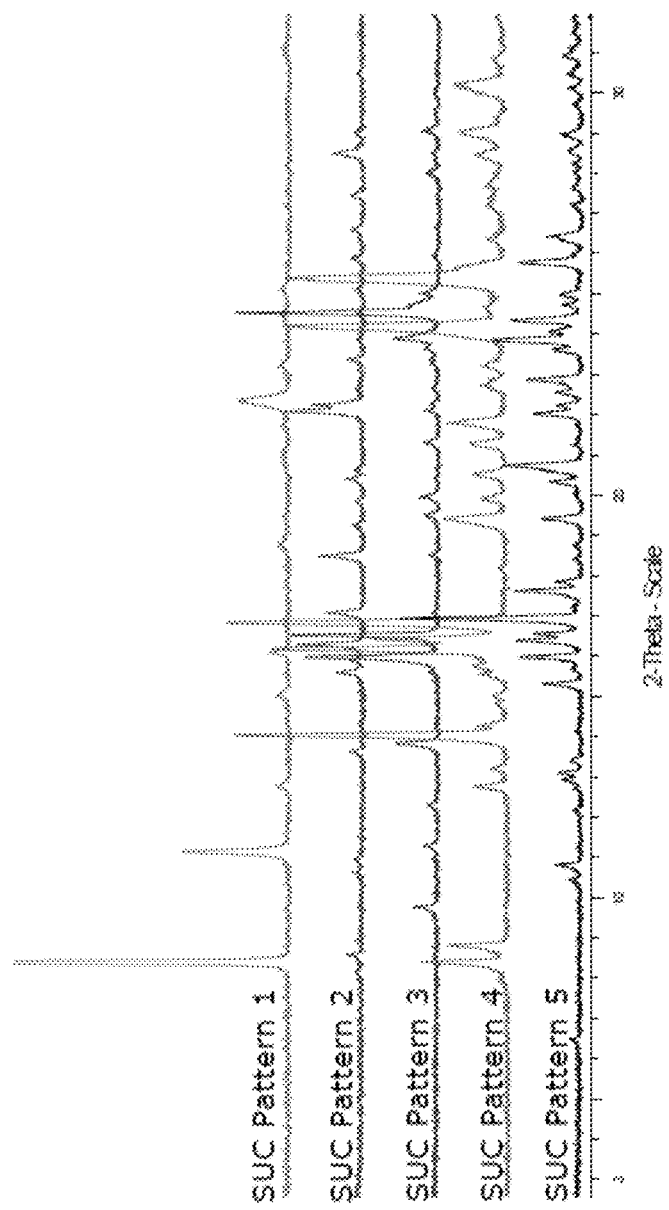
FIG. 5 shows the XRPD pattern of psilocin succinate after 7 days of static storage at 40° C. and 75% relative humidity having SUC Pattern 5 (bottom scan).
Figure 10:
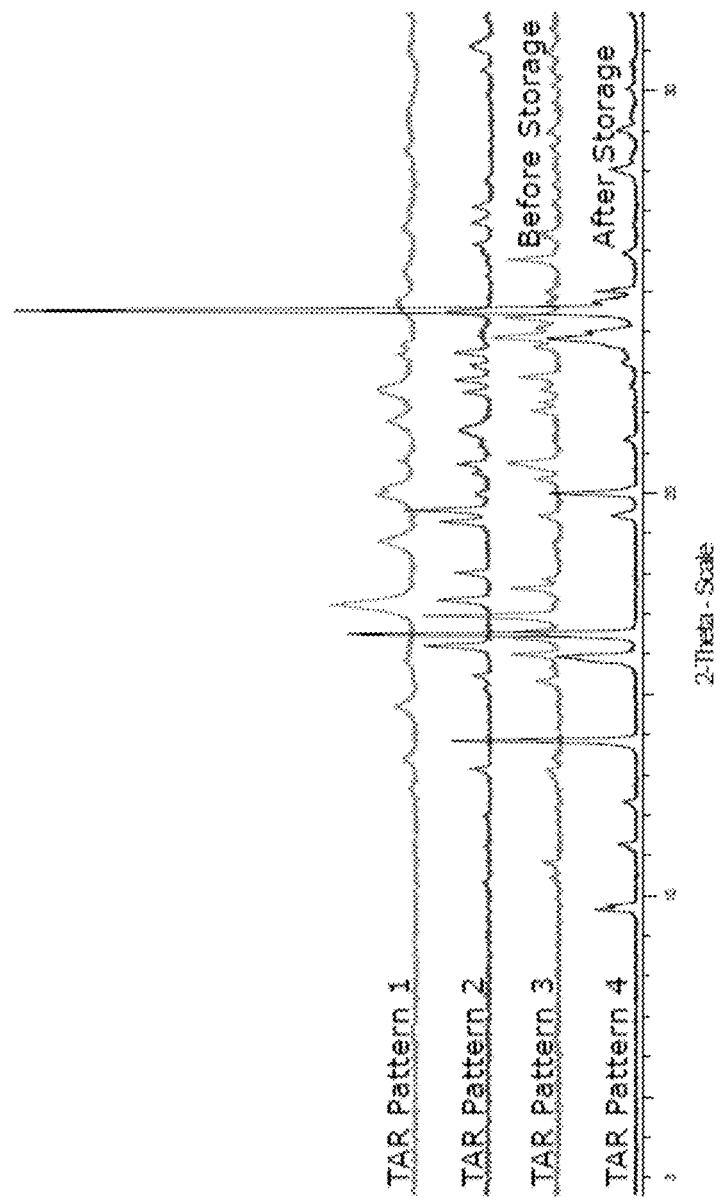
FIG. 10 shows the XRPD pattern of TAR Pattern 4 from psilocin tartrate (bottom scan) after static storage at 40° C. and a relative humidity of 75%.

| | Psilocin succinate | Psilocin tartrate |
|---|---|---|
| XRPD | SUC Pattern 4 (FIG. 4) | TAR Pattern 3 (FIG. 9) |
| HPLC | 99.1% | 98.3% |
| ¹H-NMR | Consistent with structure. 0.5 mol eq. of succinate. 0.61 mol eq. of acetone | Consistent with structure. 1 mol eq. of tartrate. 0.03 mol eq. of ethanol |
| Thermal (TGA/DSC) | 8.9% mass loss over 2 events. (8.9% = 0.61 mol eq. acetone). DSC contains two endotherms associated with the mass loss events, onset 89.3° C. (26 J/g) and 112.7° C. (56 J/g) respectively. There is a third large sharp endotherm, onset 181.3° C. (81 J/g) after which decomposition starts. | Mass loss of 4.4 wt. % (0.91 mol eq. water) associated with a broad endotherm in the DSC, onset 56.6° C. (106 J/g). Large sharp endotherm, onset 168.0° C. (125 J/g). |
| Static Storage 40° C./75% RH | XRPD - SUC Pattern 5 (FIG. 5) HPLC - 99.4% | XRPD - TAR Pattern 4 (FIG. 10) HPLC - 99.3% |

A second attempt at 100 mg scale-up for the solubility assessment was made; the results of which are summarized in Tables 7 and 8. These attempts were made as the first attempt did not give the target form (Table 5). Psilocin succinate was made in a 20 mL vial using 100 mg of psilocin free base which was dissolved in 30 volumes of acetone at 25° C. To this solution, 1.1 molar equivalents of succinic acid (1M in THF) was added. The crystallization solution was then cooled to 5° C. at a rate of 0.25° C./min giving a white suspension. To this suspension, a further 0.55 molar equivalents of succinic acid was added. The suspension was stirred for 12 hours at 5° C. The resulting white suspension was isolated using positive pressure using a fritted filter cartridge resulting in a yield of 65.8 mg.

Psilocin salicylate was made in a 20 mL vial by adding 100 mg of psilocin free base was dissolved in 30 volumes of 2-MeTHF at 25° C. To this solution, 1.1 molar equivalents of salicylic acid (1M in THF) was added. The crystallization solution was then cooled to 5° C. at a rate of 0.25° C./min. At 23° C., the crystallization started to look hazy, and about 2 mg of seed material was added. Desupersaturation to a thick white suspension was observed. At 5° C. an additional 0.55 molar equivalent of salicylic acid was added, and the crystallization solution was held at 5° C. for 12 hours. The white suspension was isolated using positive pressure using a fritted filter cartridge, which resulted in a yield of 90.35 mg.

Psilocin tartrate was made in a 20 mL vial by adding 100 mg of psilocin free base which was dissolved in 40 volumes of EtOH:water (9:1) at 25° C. To this solution, 1.1 molar equivalents of L-tartaric acid (1M in THF) was added. About 2 mg of seed material was added, sustained along with mild desupersaturation. The crystallization solution was cooled to 5° C. at a rate of 0.25° C./min and held there for 12 hours. The white suspension was isolated using positive pressure using a fritted filter cartridge, and resulted in a yield of 107.18 mg.

TABLE 7

Characterization of psilocin salts after 100 mg scale up 2ⁿᵈ attempt

| | Target | XRPD | ¹H-NMR | HPLC Purity |
|---|---|---|---|---|
| Psilocin succinate | SUC Pattern 1 | SUC Pattern 3** (Also obtained from static storage of SUC Pattern 1 and Pattern 2) | Consistent with structure. 0.5 mol eq. of succinate. Trace acetone | 99.4% |
| Psilocin salicylate | SAL Pattern 2 | SAL Pattern 1* | Consistent with structure. 1 mol eq. of salicylate. Trace THF and 2-MeTHF. | 98.9% |

TABLE 7-continued

Characterization of psilocin salts after 100 mg scale up 2$^{nd}$ attempt

Figure 12:
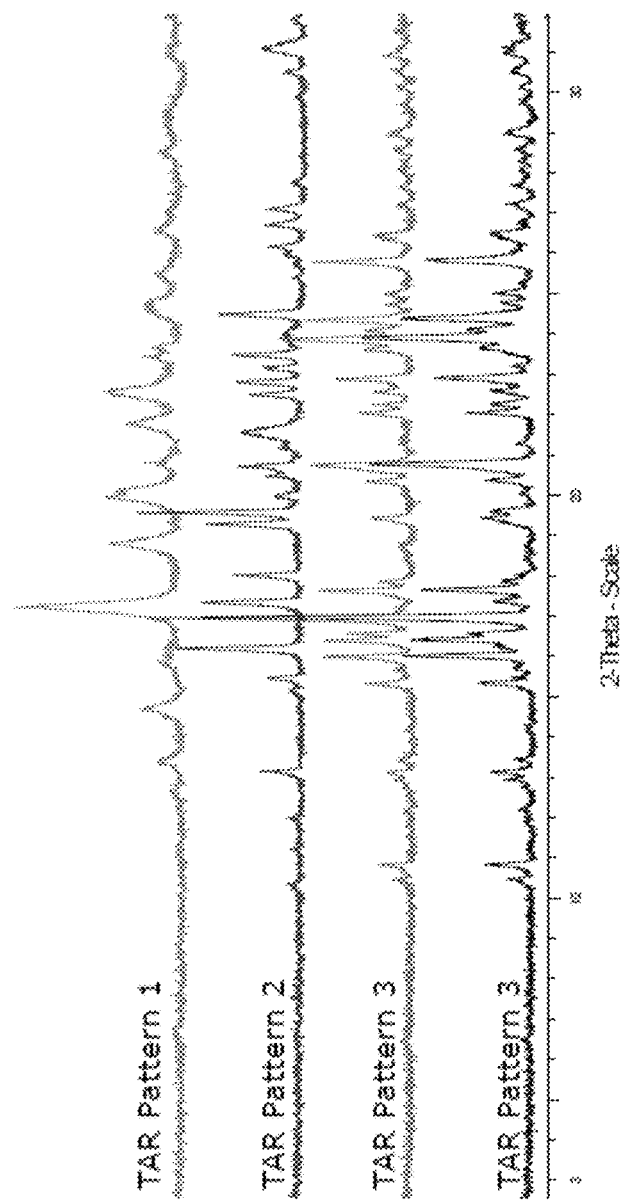
FIG. 12 shows the XRPD of psilocin tartrate with TAR Pattern 3 made using seed material from a psilocin salt having TAR Pattern 2 (bottom scan).

|  | Target | XRPD | $^1$H-NMR | HPLC Purity |
|---|---|---|---|---|
| Psilocin tartrate | TAR Pattern 2 | TAR Pattern 3* (FIG. 12) | Consistent with structure. 1 mol eq. of tartrate. Trace ethanol. | 98.4% |

*Previously characterized form
**Uncharacterized form

TABLE 8

Characterization of the isolated solid after 100 mg scale up 2nd attempt

Figure 11:
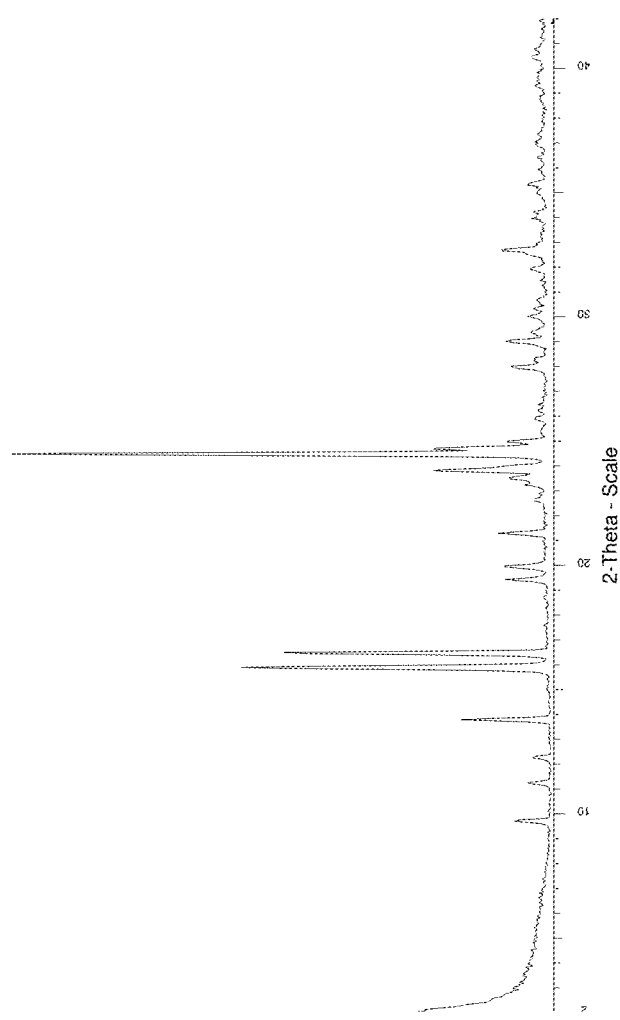
FIG. 11 shows the XRPD of the SUC Pattern 3 from psilocin succinate crystalline solid.

|  | Psilocin succinate |
|---|---|
| XRPD | SUC Pattern 3 (FIG. 11) |
| HPLC | 99.4% |
| $^1$H-NMR | Consistent with structure. 0.5 mol eq. of succinate. Trace acetone |
| Thermal (TGA/DSC) | No mass loss up until decomposition at 190° C. Sharp endotherm, onset 187.2° C. (125 J/g). This endotherm is present, at slightly lower temperatures, in the DSC data for the other three succinate patterns (two solvates and a hydrate) and suggests that the other succinate forms are dehydrating to this one. This is further supported by the static storage conversion of SUC Pattern 1 and P2 to SUC Pattern 3. |

Example 3. Solubility of Psilocin Salts in Saline

A sufficient amount of sample was suspended in 0.5 mL of media for a maximum anticipated concentration of 10 mg/mL of psilocin free base. The resulting suspensions were then shaken at 25° C. and 750 rpm for 5 hours. After equilibration, the appearance was noted, and the pH of the saturated solution was measured. Samples were then centrifuged for 2 min at 13,400 rpm, before dilution with buffer as appropriate.

Quantitation was performed by HPLC with reference to a standard solution of approximately 0.15 mg/mL. Different volumes of the standard, diluted, and undiluted sample solutions were injected. The solubility was calculated using the peak areas determined by integration of the peak found at the same retention time as the principal peak in the standard injection.

Solid residue from samples that did not fully dissolve were analyzed by XRPD to assess whether they changed form. The appearance of each sample, pH after 5 hours, XRPD of any residue, the solubility, and the averages solubility were assessed for each salt and summarized in Tables 9 and 10.

TABLE 9

Summary of solubility of psilocin and psilocin salts in saline

Figure 13:
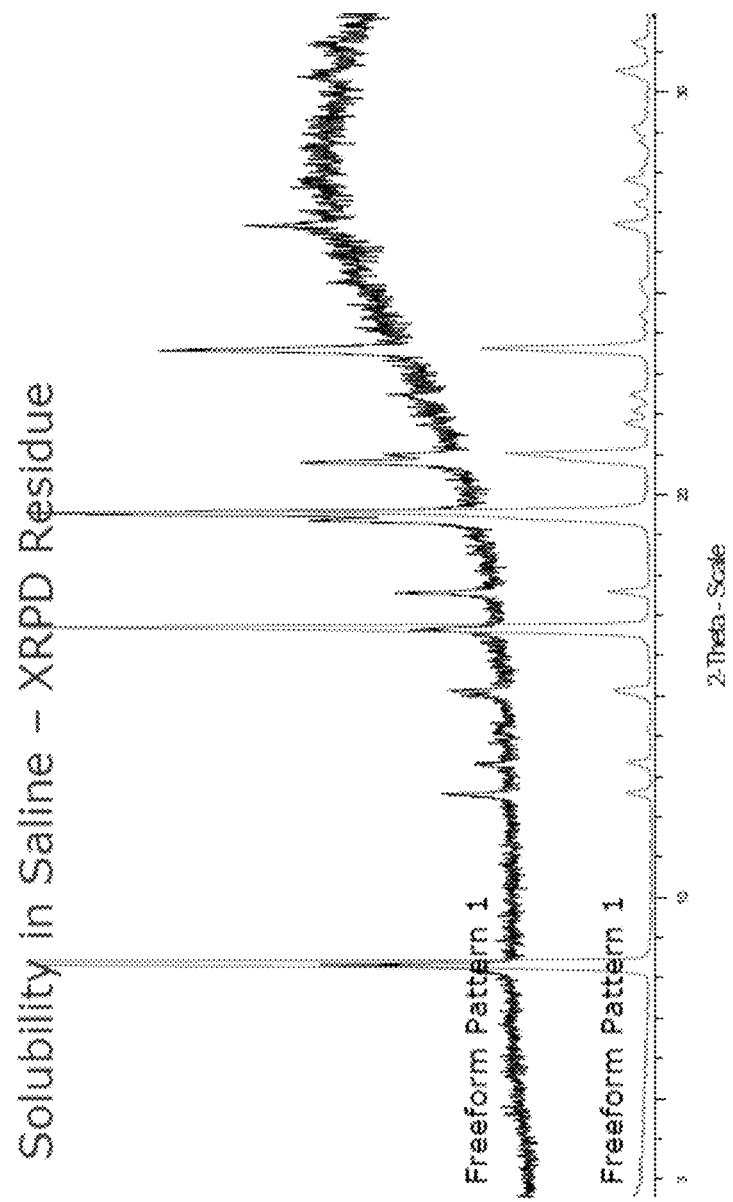
FIG. 13 shows the XRPD of the Free base Psilocin Pattern 1 from the crystalline solid remaining after dissolution in saline solution.
Figure 14:
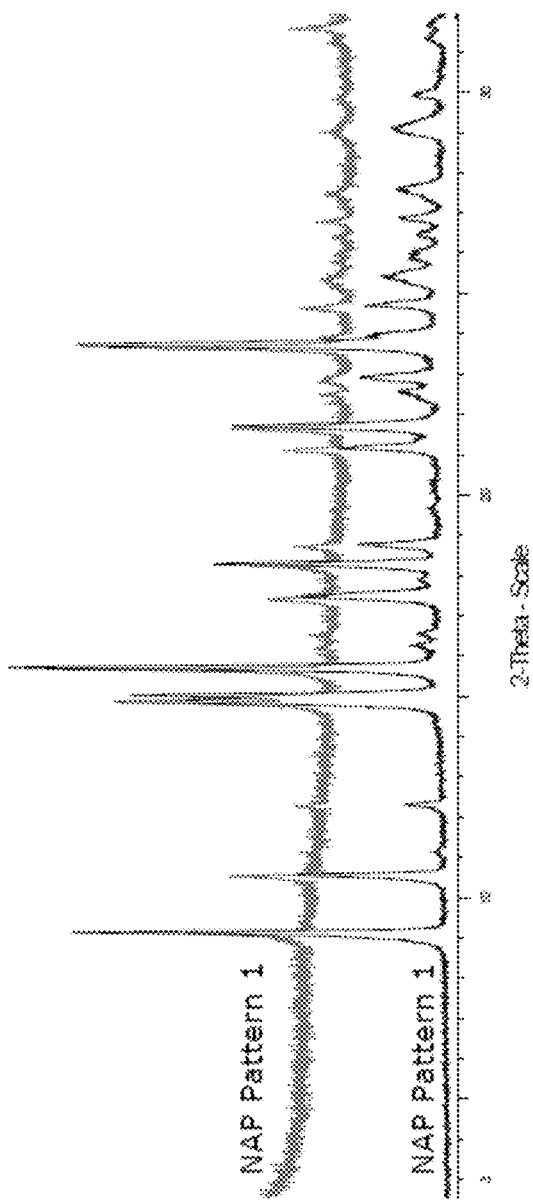
FIG. 14 shows the XRPD of the NAP Pattern 1 from the crystalline solid remaining after dissolution in saline solution.
Figure 15:
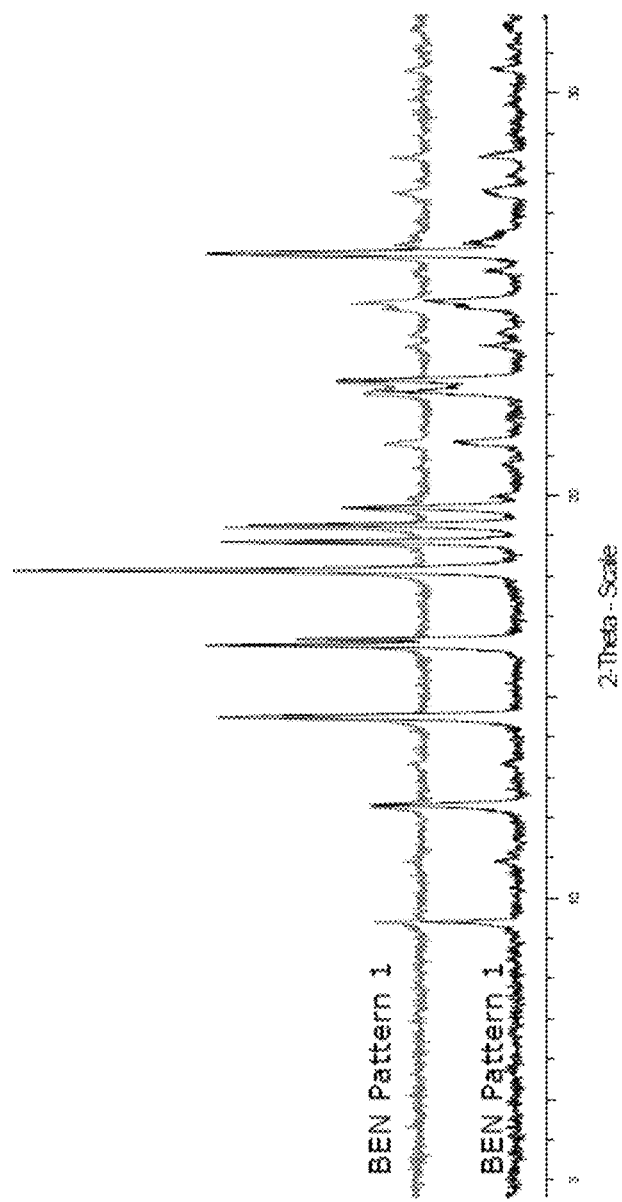
FIG. 15 shows the XRPD of the BEN Pattern 1 from the crystalline solid remaining after dissolution in saline solution.

| Sample | Form | Appearance at 5 hrs | pH at 5 hrs | XRPD of Residue | Solubility (mg/mL) | Average Solubility (mg/mL) |
|---|---|---|---|---|---|---|
| Psilocin free base | Freeform | Grey suspension | 9.8 | Freeform Pattern 1 | 0.78 | 0.76 |
| Psilocin free base | Pattern 1 | Grey suspension | 9.9 | (FIG. 13) | 0.74 |  |
| Psilocin salicylate | SAL Pattern 1 | Grey suspension | 4.2 | SAL Pattern 1 | 6.0 | 5.8 |
| Psilocin salicylate |  | Grey/blue suspension | 4.2 |  | 5.5 |  |
| Psilocin tartrate | TAR Pattern 1 | Clear solution | 3.4 | — | >10 | >10 |
| Psilocin tartrate |  | Clear solution | 3.4 |  | >10 |  |
| Psilocin 1,5-napthalenedisulfonate | NAP Pattern 1 | Grey/green suspension | 2.0 | NAP Pattern 1 (FIG. 14) | 7.0 | 7.1 |
| Psilocin 1,5-napthalenedisulfonate |  | Grey/green suspension | 2.0 |  | 7.1 |  |
| Psilocin benzoate | BEN Pattern 1 | Grey suspension | 6.8 | BEN Pattern 1 | 5.0 | 5.0 |
| Psilocin benzoate |  | Grey suspension | 6.9 | (FIG. 15) | 4.9 |  |
| Psilocin tartrate | TAR Pattern 3 | Clear solution | 3.4 | — | >10 | >10 |
| Psilocin tartrate |  | Clear solution | 3.4 |  | >10 |  |
| Psilocin hydrochloride | HCl Pattern 1 | Clear solution | 6.0 | — | >10 | >10 |
| Psilocin hydrochloride |  | Clear solution | 6.1 |  | >10 |  |
| Psilocin succinate | SUC Pattern 3 | Clear solution | 6.5 | — | >10 | >10 |
| Psilocin succinate |  | Clear solution | 6.4 |  | >10 |  |

TABLE 10

Updated summary of solubility of psilocin and psilocin salts in saline

| Sample | Form | Media | Appearance at 5 hrs | pH at 5 hrs | Solubility (mg/mL) | Average Solubility (mg/mL) |
|---|---|---|---|---|---|---|
| Psilocin free base | Freeform psilocin | Saline | Grey suspension | 9.8 | 0.78 | 0.76 |
| Psilocin free base | | | Grey suspension | 9.9 | 0.74 | |
| Psilocin salicylate | SAL Pattern 1 | | Grey suspension | 4.2 | 6.0 | 5.8 |
| Psilocin salicylate | | | Grey/blue suspension | 4.2 | 5.5 | |
| Psilocin tartrate | TAR Pattern 1 | | Fine suspension - almost clear | 3.5 | 62 | 64 |
| Psilocin tartrate | | | Fine suspension - almost clear | 3.5 | 65 | |
| Psilocin 1,5-napthalenedisulfonate | NAP Pattern 1 | | Grey/blue suspension | 2.0 | 7.0 | 7.1 |
| Psilocin 1,5-napthalenedisulfonate | | | Grey/blue suspension | 2.0 | 7.1 | |
| Psilocin benzoate | BEN Pattern 1 | | Grey suspension | 6.8 | 5.0 | 5.0 |
| Psilocin benzoate | | | Grey suspension | 6.9 | 4.9 | |
| Psilocin tartrate | TAR Pattern 3 | | Clear solution | 3.5 | 32 | Approx. 35 |
| Psilocin tartrate | | | Clear solution | 3.5 | 33 | |
| Psilocin hydrochloride | HCl Pattern 1 | | Fine suspension - almost clear | 4.0 | 36 | Approx. 36 |
| Psilocin hydrochloride | | | Fine suspension - almost clear | 5.4 | 35 | |
| Psilocin succinate | SUC Pattern 3 | | Clear solution | 6.4 | >28 | >27 |
| Psilocin succinate | | | Clear solution | 6.5 | >25 | |

TAR Pattern 1 was obtained from acetone for psilocin tartrate. The $^1$H-NMR spectroscopy suggests that TAR Pattern 1 is a mono-L-tartrate salt. The form was stable to storage at 40° C./75% RH. The solubility in saline is >10 mg/mL. The purity uplift for psilocin from the formation of TAR Pattern 1 is the lowest of the scaled-up salt forms.

SUC Pattern 3 was obtained from acetone for psilocin succinate, using a total of 1.65 mole equivalents of succinic acid. However, from $^1$H-NMR spectroscopy the solid-form only contains 0.5 mole equivalents of succinate. The thermal data suggest the form is anhydrous. SUC Pattern 1 and SUC Pattern 2 have both been observed to convert to SUC Pattern 3 at elevated temperature and humidity static storage conditions as well as possible conversion to SUC Pattern 3 at elevated temperatures observed in the DSC data, evidenced by an endotherm common to all three forms at ca. 185° C. The solubility of SUC Pattern 3 was shown to be >10 mg/mL in saline.

Although showing high solubilities (>10 mg/mL) TAR Pattern 3 and HCl Pattern 1 were not stable when stored at 40° C./75% RH, thus are not recommended to take forward. SAL Pattern 1, NAP Pattern 1 and BEN Pattern 1 all have substantial increases in solubility compared with the free-form but lower solubilities than the other salt forms. They are all stable at high temperature and humidity and have good HPLC purity uplifts.

SAL Pattern 1 and BEN Pattern 1 are anhydrous whilst NAP Pattern 1 is a likely hemihydrate. Only one benzoate salt solid form has been identified throughout this screen (two for NAP and two for SAL).

The peaks observed from XRPD for TAR Pattern 1 from psilocin tartrate (FIG. 6), SUC Pattern 3 from psilocin succinate (FIG. 11), and BEN Pattern 1 from psilocin benzoate (FIG. 8) are summarized in Table 11.

TABLE 11

Summary of XRPD Peaks

| Psilocin tartrate: TAR Pattern 1 | | Psilocin succinate: SUC Pattern 3 | | Psilocin benzoate: BEN Pattern 1 | |
|---|---|---|---|---|---|
| Angle/°2θ | Intensity/% | Angle/°2θ | Intensity/% | Angle/°2θ | Intensity/% |
| 6.7 | 8.8 | 9.7 | 7.1 | 9.4 | 17.0 |
| 12.6 | 7.9 | 11.2 | 4.7 | 10.9 | 4.9 |
| 13.4 | 15.9 | 12.3 | 3.7 | 12.3 | 24.7 |
| 14.7 | 25.0 | 13.8 | 16.9 | 13.3 | 5.6 |
| 15.8 | 13.1 | 15.9 | 57.4 | 14.5 | 54.3 |
| 16.2 | 10.5 | 16.4 | 49.6 | 15.3 | 3.4 |
| 17.2 | 100.0 | 19.4 | 8.9 | 16.3 | 82.7 |
| 18.8 | 50.5 | 20.0 | 9.0 | 16.4 | 37.8 |
| 19.9 | 52.0 | 21.3 | 10.0 | 18.2 | 100.0 |
| 20.8 | 20.1 | 22.6 | 3.5 | 18.9 | 71.1 |
| 21.8 | 49.1 | 23.3 | 5.3 | 19.3 | 46.1 |
| 22.5 | 66.6 | 23.5 | 8.0 | 19.7 | 40.7 |
| 23.4 | 28.0 | 23.8 | 22.1 | 20.0 | 7.9 |
| 23.7 | 26.0 | 24.5 | 100.0 | 20.8 | 5.0 |
| 24.7 | 34.6 | 24.7 | 22.1 | 21.3 | 16.7 |
| 25.5 | 25.1 | 25.0 | 9.0 | 21.9 | 4.9 |
| 26.5 | 26.0 | 28.0 | 7.7 | 22.6 | 42.2 |
| 27.0 | 16.9 | 28.3 | 3.4 | 22.9 | 45.3 |
| 27.4 | 11.6 | 29.0 | 8.7 | 23.8 | 14.2 |
| 28.5 | 23.0 | 29.4 | 4.1 | 24.1 | 8.2 |
| 29.4 | 20.9 | | | 24.9 | 29.3 |
| | | | | 25.6 | 11.4 |
| | | | | 26.0 | 74.3 |
| | | | | 26.3 | 19.2 |
| | | | | 26.5 | 9.8 |
| | | | | 26.9 | 5.6 |
| | | | | 27.5 | 14.7 |
| | | | | 28.5 | 17.6 |

Example 4 Photostability of Psilocin Salts

Photostability experiments were performed on approximately 3 mm depth of the solid psilocin salt material, including psilocin tartrate, psilocin benzoate, and psilocin succinate, and a solution of 0.2 mg/mL of the free base in water. Before dissolution the water was purged with nitrogen for 30 minutes to prevent oxidative degradation. Duplicate vials were prepared for each sample, where one was exposed to light and the other to act as a control, which was wrapped in foil for the duration of the experiment. The light stability test was performed using an Atlas Suntest CPS+. The sample were exposed at an iridescence level of 500 W/m² (300-800 nm) for the equivalent of 1 week of Miami sunlight, which was a total of 6.9 hours of exposure. Observations were made before and after the exposure for the free base psilocin salt, psilocin tartrate salt, psilocin succinate salt, and psilocin benzoate salt (Table 12). The purity analysis was performed post exposure for all samples at 0.2 mg/mL of the free base using an Agilent 1260 series HPLC with OpenLab software. The X-ray powder diffraction was performed on the solid psilocin salt samples before and after exposure.

The purity and stability of the solid samples after light exposure did not change when compared to pre-exposure. The XRPD analysis also found that all the samples did not change crystal form after the photostability experiments.

The psilocin benzoate salt, psilocin tartrate salt, and psilocin succinate salt when tested after dissolving in solution, all showed a greater stability in the presence of light in comparison to free base psilocin. The psilocin salt solutions were observed to change color upon exposure to light. Additionally, the purity of the free base in solution post exposure was 34.1% by HPLC, while the salt forms retained purity >75% by HPLC after light exposure. The L-tartaric acid salt form in solution was the most light-stable psilocin salt in solution with a purity of 93.2% by HPLC after exposure. The tartaric acid salt performed the best with respect to light stability as a solution, with the psilocin benzoate and psilocin succinate performing better than the free base.

Example 5. Forced Degradation of Psilocin Salts

A test was created to assess the stability of the psilocin salts and free base psilocin to oxidative degradation. Forced degradation of the psilocin salts was performed in 0.3% $H_2O_2$ to test the oxidative stability of each salt form. The appropriate volume of 0.3% $H_2O_2$ was added to the pre-weighed sample of psilocin salt in an amber vial to give a maximum concentration of 0.2 mg/mL of psilocin (free base equivalent). The samples were stored at 25° C. and the purity of each sample was assessed at 0, 1, 6, and 24 hours (Table 12). The purity analysis was performed using an Agilent 1260 series HPLC with OpenLab software.

TABLE 12

Purity Analysis of Forced Degradation of Psilocin Salts with $H_2O_2$

| | | | Water – Purity (%) | | | | Difference |
| --- | --- | --- | --- | --- | --- | --- | --- |
| Sample Id | Form | Solvent | T = 0 Hr | T = 1 Hr | T = 6 Hr | T = 24 Hr | between T 0 and T 24 (%) |
| ALB-1969-16 | Free Base | 0.3% $H_2O_2$ | 95.0 | 88.3 | 73.4 | N/A* | — |
| DR-1968-73-01 | L-Tartaric Acid | 0.3% $H_2O_2$ | 95.8 | 95.3 | 75.6 | 31.0 | 64.8 |
| DR-1968-73-02 | Succinic Acid | 0.3% $H_2O_2$ | 98.8 | 98.6 | 96.3 | 84.0 | 14.8 |
| DR-1968-78-01 | Benzoic Acid | 0.3% $H_2O_2$ | 99.0 | 98.6 | 98.5 | 85.1 | 13.9 |

In 0.3% (v/v) $H_2O_2$ the rate of degradation was slowed for the psilocin salt forms compared to free base psilocin. Of the three psilocin salts tested, the L-tartaric acid salt degraded faster than the succinic acid and benzoic acid salts. Following 6 hours of exposure to oxidizing conditions, the benzoate salt exhibited the highest stability to oxidative degradation.

These data suggest that the psilocin benzoate and psilocin succinate salts are preferred salt forms for producing a pharmaceutical composition with superior shelf-life stability, and resistance to oxidative degradation.

What is claimed is:

1. Psilocin 1:1 benzoate salt.

2. A pharmaceutical composition comprising the psilocin 1:1 benzoate salt of claim 1 and a pharmaceutically acceptable excipient.

3. The pharmaceutical composition of claim 2, comprising (i) an aqueous solution having a pH of between about 3 and about 9 and (ii) between about 0.1 mg/mL and about 50 mg/mL of the psilocin 1:1 benzoate salt.

4. A method of treating a disease or condition in a subject in need thereof, the method comprising administering to the subject a pharmaceutical composition of claim 2 in an amount sufficient to treat the disease or condition, wherein the disease or condition is lung inflammation, neuroinflammation, rheumatoid arthritis, atherosclerosis, psoriasis, type II diabetes, inflammatory bowel disease, Crohn's disease, multiple sclerosis, septicemia, chronic obstructive pulmonary disease, stroke, a traumatic brain injury, spinal cord injury, chronic pain, depression, anxiety, addiction, post-traumatic stress disorder, an eating disorder, compulsive behavior, Huntington's disease, or Parkinson's disease.

5. The method of claim 4, wherein the disease or condition is lung inflammation, neuroinflammation, psoriasis, type II diabetes, inflammatory bowel disease, Crohn's disease, multiple sclerosis, and/or septicemia.

6. The method of claim 4, wherein the disease or condition is chronic obstructive pulmonary disease (COPD).

7. The method of claim 4, wherein the disease or condition is a stroke, a traumatic brain injury, or a spinal cord injury.

8. The method of claim 4, wherein the disease or condition is chronic pain.

9. The method of claim 8, wherein the chronic pain results from post-operative pain, tension headaches, chronic lower back pain, fibromyalgia, nephropathy, multiple sclerosis, shingles, complex regional pain syndrome, cephalic pain, or sciatica.

10. The method of claim 9, wherein the chronic pain condition results from trigeminal autonomic cephalalgia.

11. The method of claim 10, wherein the trigeminal autonomic cephalalgia is selected from the group consisting of episodic and chronic cluster headache (CH), episodic and chronic paroxysmal hemicrania (PH), and short-lasting unilateral neuralgiform headache attacks with conjunctival injection and tearing (SUNCT).

12. The method of claim 11, wherein the trigeminal autonomic cephalalgia is episodic or chronic CH.

13. The method of claim 4, wherein the disease or condition is depression, anxiety, addiction, post-traumatic stress disorder, an eating disorder, or compulsive behavior.

14. The method of claim 13, wherein the disease or condition is depression.

15. The method of claim 13, wherein the disease or condition is anxiety.

16. The method of claim 4, wherein the disease or condition is Huntington's disease or Parkinson's disease.

17. The pharmaceutical composition of claim 3, comprising (i) an aqueous solution having a pH of 4±1 or 5±1 and (ii) between about 0.1 mg/mL and about 1.0 mg/mL of the psilocin 1:1 benzoate salt.

* * * * *